US012582433B2

(12) United States Patent
Berrada et al.

(10) Patent No.: US 12,582,433 B2
(45) Date of Patent: Mar. 24, 2026

(54) THROMBUS REMOVAL SYSTEMS AND ASSOCIATED METHODS

(71) Applicant: SHIFAMED HOLDINGS, LLC, Campbell, CA (US)

(72) Inventors: Marwan Berrada, Campbell, CA (US); Amr Salahieh, Saratoga, CA (US); Tom Saul, Portland, OR (US); Aadel Al-Jadda, San Carlos, CA (US)

(73) Assignee: Shifamed Holdings, LLC, Campbell, CA (US)

( * ) Notice: Subject to any disclaimer, the term of this patent is extended or adjusted under 35 U.S.C. 154(b) by 285 days.

(21) Appl. No.: 17/905,671

(22) PCT Filed: Mar. 4, 2021

(86) PCT No.: PCT/US2021/020915
§ 371 (c)(1),
(2) Date: Sep. 6, 2022

(87) PCT Pub. No.: WO2021/178696
PCT Pub. Date: Sep. 10, 2021

(65) Prior Publication Data
US 2023/0346416 A1      Nov. 2, 2023

Related U.S. Application Data

(60) Provisional application No. 63/050,039, filed on Jul. 9, 2020, provisional application No. 62/984,918, filed on Mar. 4, 2020.

(51) Int. Cl.
| | |
|---|---|
| *A61B 17/3203* | (2006.01) |
| *A61B 17/00* | (2006.01) |
| *A61B 17/3205* | (2006.01) |

(52) U.S. Cl.
CPC .. *A61B 17/32037* (2013.01); *A61B 17/32056* (2013.01); *A61B 2017/00539* (2013.01); *A61B 2017/00778* (2013.01)

(58) Field of Classification Search
CPC ........ A61B 17/22031; A61B 17/22032; A61B 17/32037; A61B 17/32056;
(Continued)

(56) References Cited

U.S. PATENT DOCUMENTS

| | | |
|---|---|---|
| 4,006,745 A | 2/1977 | Sorenson et al. |
| 5,114,581 A | 5/1992 | Goldsmith et al. |

(Continued)

FOREIGN PATENT DOCUMENTS

| | | |
|---|---|---|
| CN | 102727643 A | 10/2012 |
| CN | 105559854 A | 5/2016 |

(Continued)

OTHER PUBLICATIONS

Al-Jadda et al.; U.S. Appl. No. 18/562,038 entitled "Thrombus removal systems and associated methods," filed Nov. 17, 2023.

(Continued)

*Primary Examiner* — Jocelin C Tanner
(74) *Attorney, Agent, or Firm* — Shay Glenn LLP

(57) ABSTRACT

The present technology relates to systems and methods for removing a thrombus from a blood vessel of a patient. In some embodiments, the present technology is directed to systems including an elongated catheter having a distal portion configured to be positioned within the blood vessel of the patient, a proximal portion configured to be external to the patient, and a lumen extending therebetween. The system can also include an imaging element at the distal portion, an illumination source at the distal portion, a capture element at the distal portion and configured to engage the thrombus, a fluid delivery mechanism within the (Continued)

lumen and configured to apply fluid to (1) at least partially fragment the thrombus and (2) provide an optical path for the imaging element, and an aspiration mechanism fluidly coupled to the lumen and configured to aspirate the fragmented thrombus.

15 Claims, 7 Drawing Sheets

(58) Field of Classification Search
CPC ........ A61B 17/320758; A61B 17/3203; A61B 90/37; A61B 2017/00022; A61B 2017/00026; A61B 2017/003; A61B 2017/00539; A61B 2017/00685; A61B 2017/00778; A61B 2017/00809; A61B 2017/22079; A61B 2017/22082; A61B 2017/22084; A61B 2217/007; A61B 2218/001; A61M 1/71; A61M 1/84; A61M 1/774; A61M 3/0283; A61M 5/16827; A61F 5/442
USPC ........................................................ 606/159
See application file for complete search history.

(56) References Cited

U.S. PATENT DOCUMENTS

| | | | |
|---|---|---|---|
| 5,135,482 A | 8/1992 | Neracher |
| 5,651,776 A | 7/1997 | Appling et al. |
| 5,662,671 A * | 9/1997 | Barbut ................. A61F 2/0105 |
| | | | 606/159 |
| 5,788,647 A | 8/1998 | Eggers |
| 5,795,322 A * | 8/1998 | Boudewijn ...... A61B 17/32037 |
| | | | 604/27 |
| 5,989,271 A | 11/1999 | Bonnette et al. |
| 5,993,469 A | 11/1999 | McKenzie et al. |
| 6,004,339 A | 12/1999 | Wijay |
| 6,053,870 A | 4/2000 | Fulton, III |
| 6,059,825 A | 5/2000 | Hobbs et al. |
| 6,074,374 A | 6/2000 | Fulton |
| 6,086,534 A | 7/2000 | Kesten |
| 6,283,950 B1 | 9/2001 | Appling |
| 6,287,333 B1 | 9/2001 | Appling et al. |
| 6,306,163 B1 | 10/2001 | Fitz |
| 6,315,762 B1 | 11/2001 | Recinella et al. |
| 6,524,300 B2 | 2/2003 | Meglin |
| RE38,074 E | 4/2003 | Recinella et al. |
| 6,582,447 B1 | 6/2003 | Patel et al. |
| 6,733,489 B2 | 5/2004 | Nutting et al. |
| 6,827,701 B2 | 12/2004 | MacMahon et al. |
| 6,875,193 B1 | 4/2005 | Bonnette et al. |
| 6,881,218 B2 | 4/2005 | Beyer et al. |
| 6,942,635 B2 | 9/2005 | Rosenblatt et al. |
| 6,966,886 B2 | 11/2005 | Appling |
| 7,033,347 B2 | 4/2006 | Appling |
| 7,131,981 B2 | 11/2006 | Appling et al. |
| 7,163,533 B2 | 1/2007 | Hobbs et al. |
| 7,217,256 B2 | 5/2007 | Di Palma |
| 7,220,269 B1 | 5/2007 | Ansel et al. |
| 7,273,478 B2 | 9/2007 | Appling et al. |
| 7,279,000 B2 | 10/2007 | Cartier et al. |
| 7,344,533 B2 | 3/2008 | Pearson et al. |
| 7,347,852 B2 | 3/2008 | Hobbs et al. |
| 7,419,487 B2 | 9/2008 | Johnson et al. |
| 7,422,586 B2 | 9/2008 | Morris et al. |
| 7,455,675 B2 | 11/2008 | Schur et al. |
| 7,458,967 B2 | 12/2008 | Appling et al. |
| 7,483,457 B2 | 1/2009 | Howe et al. |
| 7,544,202 B2 | 6/2009 | Cartier et al. |
| D595,892 S | 7/2009 | Smith et al. |
| 7,563,247 B2 | 7/2009 | Maguire et al. |
| D603,044 S | 10/2009 | Appling et al. |
| 7,618,411 B2 | 11/2009 | Appling |
| 7,717,900 B2 | 5/2010 | di Palma |

| | | | |
|---|---|---|---|
| 7,722,635 B2 | 5/2010 | Beyer et al. |
| 7,740,616 B2 | 6/2010 | Smith et al. |
| 7,765,010 B2 | 7/2010 | Chornenky et al. |
| 7,766,961 B2 | 8/2010 | Patel et al. |
| 7,771,401 B2 | 8/2010 | Hekmat et al. |
| 7,780,628 B1 | 8/2010 | Keren et al. |
| D626,231 S | 10/2010 | Perchik |
| 7,826,904 B2 | 11/2010 | Appling et al. |
| 7,833,215 B2 | 11/2010 | Appling |
| RE42,016 E | 12/2010 | Chornenky et al. |
| D630,321 S | 1/2011 | Hamilton |
| D631,154 S | 1/2011 | Hamilton |
| 7,914,503 B2 | 3/2011 | Goodson et al. |
| RE42,277 E | 4/2011 | Jaafar et al. |
| 7,938,824 B2 | 5/2011 | Chornenky et al. |
| 7,942,873 B2 | 5/2011 | Kwan et al. |
| 7,947,019 B2 | 5/2011 | Perchik et al. |
| D640,788 S | 6/2011 | Appling |
| 7,993,325 B2 | 8/2011 | Elkins et al. |
| D644,735 S | 9/2011 | Elbe et al. |
| RE42,835 E | 10/2011 | Chornenky et al. |
| RE43,009 E | 12/2011 | Chornenky et al. |
| D650,475 S | 12/2011 | Smith et al. |
| 8,114,070 B2 | 2/2012 | Rubinsky et al. |
| 8,231,603 B2 | 7/2012 | Hobbs et al. |
| 8,241,343 B2 | 8/2012 | Douglass et al. |
| 8,317,773 B2 | 11/2012 | Appling et al. |
| 8,328,760 B2 | 12/2012 | Lareau |
| 8,328,768 B2 | 12/2012 | Quigley et al. |
| 8,337,451 B2 | 12/2012 | Lareau et al. |
| 8,337,470 B2 | 12/2012 | Prasad et al. |
| 8,366,687 B2 | 2/2013 | Girard et al. |
| 8,372,064 B2 | 2/2013 | Douglass et al. |
| 8,377,011 B2 | 2/2013 | Weaver et al. |
| D677,798 S | 3/2013 | Hart et al. |
| 8,425,455 B2 | 4/2013 | Nentwick |
| 8,472,011 B2 | 6/2013 | Cronin et al. |
| 8,475,488 B2 | 7/2013 | Cartier et al. |
| 8,496,644 B2 | 7/2013 | Graffam et al. |
| 8,506,512 B2 | 8/2013 | Aklog et al. |
| 8,518,011 B2 | 8/2013 | Goodson et al. |
| 8,535,306 B2 | 9/2013 | Pearson et al. |
| 8,574,204 B2 | 11/2013 | Bourne et al. |
| 8,585,678 B2 | 11/2013 | Elkins et al. |
| 8,585,950 B2 | 11/2013 | Appling et al. |
| 8,586,897 B2 | 11/2013 | Cronin |
| 8,603,070 B1 | 12/2013 | Lareau et al. |
| 8,607,428 B2 | 12/2013 | Nentwick et al. |
| 8,613,717 B2 | 12/2013 | Aklog et al. |
| 8,632,534 B2 | 1/2014 | Pearson et al. |
| 8,663,116 B2 | 3/2014 | Hamilton |
| 8,679,074 B2 | 3/2014 | Daly et al. |
| 8,734,374 B2 | 5/2014 | Aklog et al. |
| 8,734,439 B2 | 5/2014 | Gough et al. |
| 8,753,292 B2 | 6/2014 | Ingold et al. |
| 8,753,335 B2 | 6/2014 | Moshe et al. |
| 8,784,402 B1 | 7/2014 | Lareau et al. |
| 8,858,497 B2 | 10/2014 | Di Palma et al. |
| 8,864,754 B2 | 10/2014 | Appling et al. |
| 8,903,488 B2 | 12/2014 | Callas et al. |
| 8,926,573 B2 | 1/2015 | Smith et al. |
| 8,956,383 B2 | 2/2015 | Aklog et al. |
| 8,992,513 B2 | 3/2015 | Delaney |
| 9,033,914 B2 | 5/2015 | Haarala et al. |
| 9,050,435 B2 | 6/2015 | Lareau et al. |
| 9,055,964 B2 | 6/2015 | Cartier et al. |
| 9,078,665 B2 | 7/2015 | Moss et al. |
| 9,084,619 B2 | 7/2015 | Cronin et al. |
| D736,916 S | 8/2015 | Appling et al. |
| 9,149,607 B2 | 10/2015 | Scheibe et al. |
| 9,161,811 B2 | 10/2015 | Cronin |
| 9,173,704 B2 | 11/2015 | Hobbs et al. |
| 9,186,491 B2 | 11/2015 | Casiello et al. |
| D744,639 S | 12/2015 | Aklog et al. |
| 9,205,242 B2 | 12/2015 | Nardone et al. |
| 9,206,283 B1 | 12/2015 | Santerre et al. |
| D748,774 S | 2/2016 | Caron |
| 9,254,173 B2 | 2/2016 | Cronin et al. |
| 9,339,328 B2 | 5/2016 | Ortiz et al. |

(56) References Cited

U.S. PATENT DOCUMENTS

| | | |
|---|---|---|
| 9,351,861 B2 | 5/2016 | Sherburne |
| 9,358,378 B2 | 6/2016 | Hanson et al. |
| 9,402,938 B2 | 8/2016 | Aklog et al. |
| 9,408,620 B2 | 8/2016 | Rosenbluth et al. |
| 9,414,881 B2 | 8/2016 | Callas et al. |
| 9,440,046 B2 | 9/2016 | Hobbs et al. |
| 9,440,047 B1 | 9/2016 | Elberse et al. |
| 9,445,746 B1 | 9/2016 | Elberse et al. |
| 9,447,892 B2 | 9/2016 | Lareau et al. |
| 9,480,497 B2 | 11/2016 | Ingold et al. |
| 9,675,406 B2 | 6/2017 | Moss et al. |
| 9,681,909 B2 | 6/2017 | Bhargav et al. |
| 9,700,332 B2 | 7/2017 | Marchand et al. |
| 9,700,368 B2 | 7/2017 | Callas et al. |
| 9,707,339 B2 | 7/2017 | Chartrand et al. |
| 9,757,197 B2 | 9/2017 | Cronin et al. |
| 9,764,115 B2 | 9/2017 | Tegg |
| 9,788,896 B2 | 10/2017 | Cronin et al. |
| 9,789,229 B1 | 10/2017 | Lareau et al. |
| D802,409 S | 11/2017 | Caron |
| 9,820,761 B2 | 11/2017 | Garrison et al. |
| 9,867,908 B2 | 1/2018 | Lareau et al. |
| 9,888,956 B2 | 2/2018 | Model et al. |
| 9,895,189 B2 | 2/2018 | Pearson |
| 9,895,524 B2 | 2/2018 | Lareau |
| 9,907,613 B2 | 3/2018 | Cronin et al. |
| 9,933,079 B2 | 4/2018 | Weaver et al. |
| 9,999,493 B2 | 6/2018 | Nguyen et al. |
| 10,004,531 B2 | 6/2018 | Rosenbluth et al. |
| 10,010,666 B2 | 7/2018 | Rubinsky et al. |
| 10,039,900 B2 | 8/2018 | di Palma et al. |
| 10,045,790 B2 | 8/2018 | Cox et al. |
| 10,098,651 B2 | 10/2018 | Marchand et al. |
| 10,105,477 B2 | 10/2018 | Davey et al. |
| 10,159,830 B2 | 12/2018 | Miller |
| 10,166,321 B2 | 1/2019 | Casiello et al. |
| 10,188,831 B2 | 1/2019 | Elberse et al. |
| 10,238,406 B2 | 3/2019 | Cox et al. |
| D847,623 S | 5/2019 | Caron |
| 10,279,112 B2 | 5/2019 | Houde et al. |
| 10,349,960 B2 | 7/2019 | Quick |
| D860,941 S | 9/2019 | Wheeler |
| 10,429,517 B1 | 10/2019 | Isham et al. |
| 10,493,257 B2 | 12/2019 | Chartrand et al. |
| 10,500,329 B2 | 12/2019 | Weaver et al. |
| 10,517,617 B2 | 12/2019 | Aklog et al. |
| 10,517,633 B2 | 12/2019 | Nash et al. |
| D879,957 S | 3/2020 | Zabar et al. |
| 10,610,678 B2 | 4/2020 | Martin |
| 10,660,691 B2 | 5/2020 | McKernon et al. |
| 10,782,425 B2 | 9/2020 | Isham |
| 10,786,270 B2 | 9/2020 | Yang et al. |
| 10,806,896 B2 | 10/2020 | Davies et al. |
| 10,835,715 B2 | 11/2020 | Cruz et al. |
| D908,204 S | 1/2021 | Casiello et al. |
| 10,905,492 B2 | 2/2021 | Neal |
| 10,912,885 B2 | 2/2021 | Maguire et al. |
| D916,280 S | 4/2021 | Swift |
| D916,281 S | 4/2021 | Swift |
| 11,000,682 B2 | 5/2021 | Merritt et al. |
| 11,065,018 B2 | 7/2021 | Buck et al. |
| 11,154,314 B2 | 10/2021 | Quick |
| 11,241,564 B2 | 2/2022 | Casiello et al. |
| 11,259,824 B2 | 3/2022 | Brady et al. |
| 11,433,218 B2 | 9/2022 | Quick et al. |
| 11,497,889 B2 | 11/2022 | Mixter et al. |
| D972,720 S | 12/2022 | Cote et al. |
| 11,559,382 B2 | 1/2023 | Merritt et al. |
| 11,607,150 B2 | 3/2023 | Schweikert et al. |
| 11,648,020 B2 | 5/2023 | Cote et al. |
| 11,832,837 B2 | 12/2023 | Hauser |
| 11,864,779 B2 | 1/2024 | Dinh |
| 11,890,046 B2 | 2/2024 | Neal et al. |
| 11,950,835 B2 | 4/2024 | O'Brien et al. |
| 11,954,887 B2 | 4/2024 | Blau |
| 11,957,405 B2 | 4/2024 | Pearson |
| 11,986,196 B2 | 5/2024 | Wallace et al. |
| 11,986,382 B2 | 5/2024 | Merritt et al. |
| 11,992,643 B2 | 5/2024 | Lee et al. |
| 11,998,223 B2 | 6/2024 | Brady et al. |
| 12,002,065 B2 | 6/2024 | Look et al. |
| 12,004,731 B2 | 6/2024 | Duffy et al. |
| 12,016,580 B2 | 6/2024 | Quick et al. |
| 12,023,057 B2 | 7/2024 | Hauser |
| 12,023,058 B2 | 7/2024 | Casey |
| 12,029,442 B2 | 7/2024 | O'Malley |
| 12,042,160 B2 | 7/2024 | Yang et al. |
| 12,048,446 B2 | 7/2024 | Dwivedi et al. |
| 12,053,685 B2 | 8/2024 | Lockhart et al. |
| 12,076,037 B2 | 9/2024 | Brady et al. |
| 12,080,020 B2 | 9/2024 | Blau |
| 12,096,938 B2 | 9/2024 | Hettel et al. |
| 12,096,951 B2 | 9/2024 | Barry et al. |
| 12,097,345 B2 | 9/2024 | Schultz et al. |
| 12,133,657 B2 | 11/2024 | Vale et al. |
| 12,144,515 B2 | 11/2024 | Nagireiter et al. |
| 12,150,659 B2 | 11/2024 | Look et al. |
| 12,156,665 B2 | 12/2024 | Look et al. |
| 12,156,666 B2 | 12/2024 | Trosper et al. |
| 12,156,667 B2 | 12/2024 | Trosper et al. |
| 12,171,449 B2 | 12/2024 | Lee |
| 12,171,917 B1 | 12/2024 | Buck et al. |
| 12,184,353 B2 | 12/2024 | Collins |
| 12,186,064 B2 | 1/2025 | Strasser et al. |
| 12,198,330 B2 | 1/2025 | Blau |
| 12,201,506 B2 | 1/2025 | Buck et al. |
| 12,213,691 B2 | 2/2025 | Whelan |
| 12,214,189 B2 | 2/2025 | Lorenzo et al. |
| 12,220,138 B2 | 2/2025 | Whelan |
| 12,251,119 B2 | 3/2025 | Naglreiter et al. |
| 12,343,479 B2 | 7/2025 | Yang et al. |
| 12,343,486 B2 | 7/2025 | Casey et al. |
| 12,350,443 B2 | 7/2025 | Yee et al. |
| 12,369,940 B2 | 7/2025 | Jenson et al. |
| 12,376,904 B1 | 8/2025 | Stern et al. |
| 12,402,902 B2 | 9/2025 | Vale et al. |
| 12,414,784 B1 | 9/2025 | Li et al. |
| 12,419,703 B2 | 9/2025 | O'Malley et al. |
| 12,440,230 B2 | 10/2025 | Gamba et al. |
| 12,462,425 B2 | 11/2025 | Blau |
| 2002/0058904 A1 | 5/2002 | Boock et al. |
| 2002/0111579 A1 | 8/2002 | Moutafis et al. |
| 2002/0123761 A1 | 9/2002 | Barbut et al. |
| 2002/0132076 A1 | 9/2002 | Stevens |
| 2003/0236517 A1 | 12/2003 | Appling |
| 2004/0097880 A1 | 5/2004 | Schur |
| 2005/0027262 A1 | 2/2005 | Appling et al. |
| 2005/0131343 A1 | 6/2005 | Abrams et al. |
| 2005/0143687 A1 | 6/2005 | Rosenblatt et al. |
| 2005/0165364 A1 | 7/2005 | DiMatteo et al. |
| 2005/0171510 A1 | 8/2005 | DiCarlo et al. |
| 2006/0184141 A1 | 8/2006 | Smith et al. |
| 2006/0270974 A1 | 11/2006 | Goff et al. |
| 2006/0282119 A1 | 12/2006 | Perchik |
| 2006/0293725 A1 | 12/2006 | Rubinsky et al. |
| 2006/0293730 A1 | 12/2006 | Rubinsky et al. |
| 2006/0293731 A1 | 12/2006 | Rubinsky et al. |
| 2007/0021685 A1 | 1/2007 | Oepen et al. |
| 2007/0078391 A1 | 4/2007 | Wortley et al. |
| 2007/0106162 A1 | 5/2007 | Illyes et al. |
| 2007/0156135 A1 | 7/2007 | Rubinsky et al. |
| 2007/0173786 A1 | 7/2007 | Recinella et al. |
| 2007/0191825 A1 | 8/2007 | Cronin et al. |
| 2007/0198035 A1 | 8/2007 | Threlkeld |
| 2008/0114308 A1 | 5/2008 | di Palma et al. |
| 2008/0132884 A1 | 6/2008 | Rubinsky et al. |
| 2008/0132885 A1 | 6/2008 | Rubinsky et al. |
| 2008/0154186 A1 | 6/2008 | Appling et al. |
| 2008/0167649 A1 | 7/2008 | Edwards et al. |
| 2008/0167678 A1 | 7/2008 | Morsi |
| 2008/0172080 A1 | 7/2008 | Isham |
| 2008/0183202 A1 | 7/2008 | Isham |
| 2008/0208180 A1 | 8/2008 | Cartier et al. |
| 2008/0208236 A1 | 8/2008 | Hobbs et al. |

(56) References Cited

U.S. PATENT DOCUMENTS

| | | |
|---|---|---|
| 2008/0269774 A1 | 10/2008 | Garcia et al. |
| 2008/0287939 A1 | 11/2008 | Appling et al. |
| 2008/0294188 A1 | 11/2008 | Appling et al. |
| 2008/0300619 A1 | 12/2008 | Isham |
| 2009/0024190 A1 | 1/2009 | Irvine |
| 2009/0038752 A1 | 2/2009 | Weng et al. |
| 2009/0048577 A1 | 2/2009 | Gillies et al. |
| 2009/0076585 A1 | 3/2009 | Hendriksen et al. |
| 2009/0118683 A1 | 5/2009 | Hanson et al. |
| 2009/0131924 A1 | 5/2009 | Meyer et al. |
| 2009/0163926 A1 | 6/2009 | Sos |
| 2009/0171267 A1* | 7/2009 | Bonnette .......... A61B 17/32037 604/22 |
| 2009/0221899 A1 | 9/2009 | Isham |
| 2009/0259220 A1 | 10/2009 | Appling et al. |
| 2009/0281477 A1 | 11/2009 | Mikus et al. |
| 2009/0306606 A1 | 12/2009 | Lancette et al. |
| 2009/0306625 A1 | 12/2009 | Pereira-Kamath et al. |
| 2009/0314724 A1 | 12/2009 | Nierich |
| 2010/0004623 A1 | 1/2010 | Hamilton et al. |
| 2010/0022947 A1 | 1/2010 | Hassidov et al. |
| 2010/0076302 A1 | 3/2010 | Gray et al. |
| 2010/0094201 A1 | 4/2010 | Mallaby |
| 2010/0114063 A1 | 5/2010 | Recinella et al. |
| 2010/0152725 A1 | 6/2010 | Pearson et al. |
| 2010/0168642 A1 | 7/2010 | Appling et al. |
| 2010/0204712 A1 | 8/2010 | Mallaby |
| 2010/0249771 A1 | 9/2010 | Pearson et al. |
| 2010/0249815 A1 | 9/2010 | Jantzen et al. |
| 2010/0250209 A1 | 9/2010 | Pearson et al. |
| 2010/0256487 A1 | 10/2010 | Hawkins et al. |
| 2010/0256546 A1 | 10/2010 | Davis et al. |
| 2010/0256630 A1 | 10/2010 | Hamilton et al. |
| 2011/0004295 A1 | 1/2011 | Wittens |
| 2011/0034886 A1 | 2/2011 | Elbe et al. |
| 2011/0040321 A1 | 2/2011 | Cartier |
| 2011/0060316 A1 | 3/2011 | DiCarlo |
| 2011/0105823 A1 | 5/2011 | Single et al. |
| 2011/0112527 A1 | 5/2011 | Hamilton et al. |
| 2011/0172644 A1 | 7/2011 | Zanoni et al. |
| 2011/0190734 A1 | 8/2011 | Graffam et al. |
| 2011/0190806 A1 | 8/2011 | Wittens |
| 2011/0213392 A1 | 9/2011 | Aklog et al. |
| 2011/0238057 A1 | 9/2011 | Moss et al. |
| 2011/0288529 A1 | 11/2011 | Fulton |
| 2012/0059210 A1 | 3/2012 | Frassica |
| 2012/0078232 A1 | 3/2012 | Schulting |
| 2012/0101471 A1 | 4/2012 | di Palma et al. |
| 2012/0184942 A1 | 7/2012 | Lareau |
| 2012/0193255 A1 | 8/2012 | Lareau et al. |
| 2012/0226271 A1 | 9/2012 | Callas et al. |
| 2012/0310230 A1 | 12/2012 | Willis |
| 2013/0131691 A1 | 5/2013 | Kozak et al. |
| 2013/0150811 A1 | 6/2013 | Horgan |
| 2013/0304082 A1 | 11/2013 | Aklog et al. |
| 2013/0310845 A1 | 11/2013 | Thor et al. |
| 2013/0324943 A1 | 12/2013 | Weaver et al. |
| 2013/0338608 A1 | 12/2013 | Moorehead et al. |
| 2014/0005699 A1 | 1/2014 | Bonnette et al. |
| 2014/0042154 A1 | 2/2014 | Cronin |
| 2014/0074049 A1 | 3/2014 | Veldhuijzen et al. |
| 2014/0228869 A1 | 8/2014 | Bonnette et al. |
| 2014/0303658 A1* | 10/2014 | Bonnette .......... A61B 17/32075 606/159 |
| 2014/0364896 A1 | 12/2014 | Consigny |
| 2015/0057648 A1 | 2/2015 | Swift et al. |
| 2015/0068941 A1 | 3/2015 | Caron |
| 2015/0150589 A1 | 6/2015 | Yamanouchi |
| 2015/0190615 A1 | 7/2015 | Shaltis |
| 2015/0230810 A1 | 8/2015 | Creighton et al. |
| 2015/0272622 A1* | 10/2015 | Carson ................. C12Q 1/6883 514/10.5 |
| 2015/0305810 A1 | 10/2015 | McElwee et al. |
| 2015/0320488 A1 | 11/2015 | Moshe et al. |
| 2015/0359547 A1 | 12/2015 | Vale et al. |
| 2016/0022371 A1 | 1/2016 | Sauer et al. |
| 2016/0030708 A1 | 2/2016 | Casiello et al. |
| 2016/0038174 A1 | 2/2016 | Bruzzi et al. |
| 2016/0058493 A1 | 3/2016 | Neal et al. |
| 2016/0106501 A1 | 4/2016 | Appling |
| 2016/0114128 A1 | 4/2016 | Lancette |
| 2016/0114129 A1 | 4/2016 | Lancette |
| 2016/0135712 A1 | 5/2016 | Holochwost et al. |
| 2016/0135829 A1 | 5/2016 | Holochwost et al. |
| 2016/0235974 A1 | 8/2016 | Holochwost et al. |
| 2016/0271321 A1 | 9/2016 | Chambers et al. |
| 2016/0317797 A1 | 11/2016 | Smith et al. |
| 2016/0346472 A1 | 12/2016 | Mitchell et al. |
| 2017/0136158 A1 | 5/2017 | Culhane et al. |
| 2017/0172603 A1 | 6/2017 | Bonnette et al. |
| 2017/0215890 A1 | 8/2017 | Trujman et al. |
| 2017/0231655 A1 | 8/2017 | Aljuri et al. |
| 2017/0303949 A1 | 10/2017 | Ribo Jacobi et al. |
| 2017/0333060 A1 | 11/2017 | Panian |
| 2017/0333076 A1 | 11/2017 | Bruzzi et al. |
| 2018/0064526 A1 | 3/2018 | Walzman |
| 2018/0071014 A1 | 3/2018 | Neal et al. |
| 2018/0071492 A1 | 3/2018 | Laby et al. |
| 2018/0098782 A1 | 4/2018 | Farago |
| 2018/0103974 A1* | 4/2018 | Osborne .............. A61B 17/221 |
| 2018/0116710 A1 | 5/2018 | Pearson |
| 2018/0207397 A1 | 7/2018 | Look et al. |
| 2018/0272050 A1 | 9/2018 | Laureau et al. |
| 2018/0291882 A1 | 10/2018 | Algawi et al. |
| 2018/0317899 A1 | 11/2018 | Zada |
| 2018/0344987 A1 | 12/2018 | Lancette et al. |
| 2019/0008550 A1 | 1/2019 | Yamanouchi |
| 2019/0021856 A1 | 1/2019 | High |
| 2019/0029791 A1 | 1/2019 | Walzman |
| 2019/0030319 A1 | 1/2019 | Raines |
| 2019/0038300 A1 | 2/2019 | Savastano et al. |
| 2019/0054284 A1 | 2/2019 | Smith et al. |
| 2019/0076623 A1 | 3/2019 | Mackay et al. |
| 2019/0083169 A1 | 3/2019 | Single et al. |
| 2019/0143085 A1 | 5/2019 | Isham |
| 2019/0167287 A1 | 6/2019 | Vale et al. |
| 2019/0175939 A1 | 6/2019 | Isham et al. |
| 2019/0217058 A1 | 7/2019 | Swift |
| 2019/0262031 A1 | 8/2019 | Efremkin |
| 2019/0290323 A1 | 9/2019 | Chun et al. |
| 2019/0321656 A1 | 10/2019 | Isham et al. |
| 2019/0365248 A1 | 12/2019 | Mueller et al. |
| 2019/0365464 A1 | 12/2019 | Govari et al. |
| 2020/0022712 A1 | 1/2020 | Deville et al. |
| 2020/0030501 A1 | 1/2020 | Minskoff |
| 2020/0038057 A1 | 2/2020 | Rai et al. |
| 2020/0054864 A1 | 2/2020 | Vrancken Peeters et al. |
| 2020/0085453 A1* | 3/2020 | Porter .............. A61M 25/0082 |
| 2020/0101326 A1 | 4/2020 | Zeringue |
| 2020/0107843 A1 | 4/2020 | Goertz et al. |
| 2020/0164117 A1 | 5/2020 | Culhane et al. |
| 2020/0246014 A1 | 8/2020 | Walzman |
| 2020/0253670 A1 | 8/2020 | Doisneau et al. |
| 2020/0276415 A1 | 9/2020 | Tang et al. |
| 2020/0281611 A1 | 9/2020 | Kelly et al. |
| 2020/0289722 A1 | 9/2020 | Culbert et al. |
| 2020/0352286 A1 | 11/2020 | Galindo et al. |
| 2020/0397959 A1 | 12/2020 | Douglas et al. |
| 2021/0001090 A1 | 1/2021 | Tran et al. |
| 2021/0008354 A1 | 1/2021 | Bhamanyar |
| 2021/0069468 A1 | 3/2021 | Keating et al. |
| 2021/0085931 A1 | 3/2021 | Green et al. |
| 2021/0121188 A1 | 4/2021 | Yurek |
| 2021/0128182 A1 | 5/2021 | Teigen et al. |
| 2021/0128893 A1 | 5/2021 | Twomey et al. |
| 2021/0145445 A9 | 5/2021 | Goldsmith |
| 2021/0153884 A1 | 5/2021 | Casey et al. |
| 2021/0154433 A1 | 5/2021 | Casey et al. |
| 2021/0186541 A1 | 6/2021 | Thress |
| 2021/0186547 A1 | 6/2021 | Kassab et al. |
| 2021/0196292 A1* | 7/2021 | Vale .................. A61M 25/0045 |
| 2021/0220006 A1 | 7/2021 | Mitchell |
| 2021/0298773 A1 | 9/2021 | Echarri et al. |
| 2021/0315639 A1 | 10/2021 | Manucherhabadi et al. |

(56) References Cited

U.S. PATENT DOCUMENTS

| | | | |
|---|---|---|---|
| 2021/0346040 A1 | 11/2021 | Panian | |
| 2021/0361314 A1 | 11/2021 | Teigen et al. | |
| 2021/0378694 A1 | 12/2021 | Thress et al. | |
| 2021/0393277 A1 | 12/2021 | Vale et al. | |
| 2022/0000500 A1* | 1/2022 | Arad Hadar | A61B 17/221 |
| 2022/0008022 A1 | 1/2022 | Raman et al. | |
| 2022/0039815 A1 | 2/2022 | Thress et al. | |
| 2022/0054151 A1 | 2/2022 | Shifflette | |
| 2022/0061870 A1 | 3/2022 | Mintz | |
| 2022/0105333 A1 | 4/2022 | Bourne et al. | |
| 2022/0125450 A1 | 4/2022 | Sirhan et al. | |
| 2022/0142638 A1 | 5/2022 | Enright et al. | |
| 2022/0151647 A1 | 5/2022 | Dolendo et al. | |
| 2022/0152355 A1 | 5/2022 | Dolendo et al. | |
| 2022/0175404 A1 | 6/2022 | Mintz et al. | |
| 2022/0193373 A1 | 6/2022 | Clark et al. | |
| 2022/0202506 A1 | 6/2022 | Sganga et al. | |
| 2022/0249151 A1 | 8/2022 | Forrest et al. | |
| 2022/0257268 A1 | 8/2022 | Culbert et al. | |
| 2022/0287729 A1 | 9/2022 | Phillips et al. | |
| 2023/0088977 A1 | 3/2023 | Fischell et al. | |
| 2023/0148876 A1 | 5/2023 | Robinson et al. | |
| 2023/0149035 A1 | 5/2023 | Sirhan et al. | |
| 2023/0285081 A1 | 9/2023 | Wagner et al. | |
| 2023/0329777 A1 | 10/2023 | Single et al. | |
| 2024/0000469 A1 | 1/2024 | Teigen et al. | |
| 2024/0074804 A1 | 3/2024 | Neal et al. | |
| 2024/0138903 A1 | 5/2024 | Pearson | |
| 2024/0156473 A1 | 5/2024 | Aklog et al. | |
| 2024/0164804 A1 | 5/2024 | Jenson et al. | |
| 2024/0164805 A1 | 5/2024 | Jenson et al. | |
| 2024/0173063 A1 | 5/2024 | Neal, II et al. | |
| 2024/0188972 A1 | 6/2024 | Vale et al. | |
| 2024/0189544 A1 | 6/2024 | Casey et al. | |
| 2024/0197349 A1 | 6/2024 | Kelly et al. | |
| 2024/0197978 A1 | 6/2024 | Yee | |
| 2024/0198060 A1 | 6/2024 | Casey et al. | |
| 2024/0198072 A1 | 6/2024 | Merritt et al. | |
| 2024/0216600 A1 | 7/2024 | Lenihan et al. | |
| 2024/0245417 A1 | 7/2024 | Baron et al. | |
| 2024/0245424 A1 | 7/2024 | Casey et al. | |
| 2024/0268844 A1 | 8/2024 | Casey et al. | |
| 2024/0285846 A1 | 8/2024 | Su et al. | |
| 2024/0299707 A1 | 9/2024 | Humbert et al. | |
| 2024/0341785 A1 | 10/2024 | Trosper et al. | |
| 2024/0341786 A1 | 10/2024 | Trosper et al. | |
| 2024/0382223 A1 | 11/2024 | Gilvarry et al. | |
| 2025/0017616 A1 | 1/2025 | Illindala | |
| 2025/0064322 A1 | 2/2025 | Vale et al. | |
| 2025/0235221 A1 | 7/2025 | Janardhan et al. | |

FOREIGN PATENT DOCUMENTS

| | | | |
|---|---|---|---|
| CN | 211068270 U | 7/2020 | |
| CN | 111481262 A | 8/2020 | |
| CN | 111528983 A | 8/2020 | |
| DE | 4018736 A1 | 1/1992 | |
| JP | H0197951 A | 4/1989 | |
| JP | 2007117384 A | 5/2007 | |
| JP | 2010505542 A | 2/2010 | |
| JP | 2010506653 A | 3/2010 | |
| JP | 2013154171 A | 8/2013 | |
| WO | WO89/05665 A2 | 6/1989 | |
| WO | WO94/016706 A1 | 8/1994 | |
| WO | WO2000/006224 A1 | 2/2000 | |
| WO | WO02/26289 A1 | 4/2002 | |
| WO | WO2003/084596 A1 | 10/2003 | |
| WO | WO2003/092537 A2 | 11/2003 | |
| WO | WO2004/000099 A2 | 12/2003 | |
| WO | WO2004/004546 A2 | 1/2004 | |
| WO | WO2004/043220 A2 | 5/2004 | |
| WO | WO2004/050144 A2 | 6/2004 | |
| WO | WO2004/093941 A2 | 11/2004 | |
| WO | WO2006/012242 A2 | 2/2006 | |
| WO | WO2006/012243 A2 | 2/2006 | |
| WO | WO2006/012244 A2 | 2/2006 | |
| WO | WO2006/086516 A2 | 8/2006 | |
| WO | WO2007/017876 A2 | 2/2007 | |
| WO | WO2007/041471 A2 | 4/2007 | |
| WO | WO2007/085025 A2 | 7/2007 | |
| WO | WO2008/124790 A2 | 10/2008 | |
| WO | WO2008/147760 A1 | 12/2008 | |
| WO | WO2009/035582 A1 | 3/2009 | |
| WO | WO2009/046439 A2 | 4/2009 | |
| WO | WO2009/062105 A2 | 5/2009 | |
| WO | WO2009/114826 A2 | 9/2009 | |
| WO | WO2009/131583 A1 | 10/2009 | |
| WO | WO2009/137800 A2 | 11/2009 | |
| WO | WO2009/155526 A2 | 12/2009 | |
| WO | WO2010/008834 A2 | 1/2010 | |
| WO | WO2010/085765 A2 | 7/2010 | |
| WO | WO2010/093692 A2 | 8/2010 | |
| WO | WO2010/117806 A1 | 10/2010 | |
| WO | WO2010/138919 A2 | 12/2010 | |
| WO | WO2011/022674 A2 | 2/2011 | |
| WO | WO2011/103096 A2 | 8/2011 | |
| WO | WO2011/103133 A2 | 8/2011 | |
| WO | WO2012/051433 A2 | 4/2012 | |
| WO | WO2013/119662 A1 | 8/2013 | |
| WO | WO2014/047626 A2 | 3/2014 | |
| WO | WO2015/196156 A1 | 12/2015 | |
| WO | WO2016/164930 A1 | 10/2016 | |
| WO | WO2017/070702 A1 | 4/2017 | |
| WO | WO2017/106877 A1 | 6/2017 | |
| WO | WO2018/033401 A1 | 2/2018 | |
| WO | WO2018/080590 A1 | 5/2018 | |
| WO | WO2018/094050 A2 | 5/2018 | |
| WO | WO2019/050765 A1 | 3/2019 | |
| WO | WO2020/036809 A1 | 2/2020 | |
| WO | WO2020/206366 A1 | 10/2020 | |
| WO | WO2021/076954 A1 | 4/2021 | |
| WO | WO2021/127202 A1 | 6/2021 | |
| WO | WO2021/178696 A1 | 9/2021 | |
| WO | WO20212/48042 A1 | 12/2021 | |
| WO | WO2022/032173 A1 | 2/2022 | |
| WO | WO2022/103848 A1 | 5/2022 | |
| WO | WO2022/109021 A1 | 5/2022 | |
| WO | WO2022/109034 A1 | 5/2022 | |
| WO | WO2022/120270 A1 | 6/2022 | |
| WO | WO2023/168415 A1 | 9/2023 | |
| WO | WO2025/050040 A1 | 3/2025 | |
| WO | WO2025/054612 A1 | 3/2025 | |
| WO | WO2025/054613 A1 | 3/2025 | |
| WO | WO2025/085924 A1 | 4/2025 | |

OTHER PUBLICATIONS

Al-Jadda et al.; U.S. Appl. No. 18/568,656 entitled "Thrombus removal systems and associated meethods," filed Dec. 8, 2023.

Al-Jadda et al.; U.S. Appl. No. 18/568,681 entitled "Thrombus removal systems and associated methods," filed Dec. 8, 2023.

Salahieh et al.; U.S. Appl. No. 18/688,941 entitled "Thrombus removal systems and associated methods," filed Mar. 4, 2024.

Tanyildizi et al.; In vitro testing of a funnel-shaped tip catheter model to decrease clot migration during mechanical thrombectomy; Scientific Reports; 10(1); 7 pages; Jan. 20, 2020.

Anenberg et al.; Optogenetic stimulation of GABA neurons can decrease local neuronal activity while increasing cortical blood flow; Journal of Cerebral Blood Flow & Metabolism; 35(10); pp. 1579-1586; Oct. 2015.

Eucker et al.; Phase plane analysis of left ventricular hemodynamics; Journal of Applied Physiology; 90(6); pp. 2238-2244; Jun. 1, 2001.

Humbert et al.; 2022 ESC/ERS Guidelines for the diagnosis and treatment of pulmonary hypertension: Developed by the task force for the diagnosis and treatment of pulmonary hypertension of the European Society of Cardiology (ESC) and the European Respiratory Society (ERS): Endorsed by the international Society for Heart and Lung Transplantation (ISHLT) and the European Reference Network on rare respiratory diseases (ERN-LUNG); European heart journal; 43(38); pp. 3618-3731; Oct. 7, 2022.

(56)        References Cited

OTHER PUBLICATIONS

Kondo et al.; Pulmonary hypertension: diagnosis, management, and treatment; Nagoya journal of medical science; 81(1); pp. 19-30; Feb. 2019.

Gunning et al.; U.S. Appl. No. 18/835,686 entitled "Thrombus removal systems and associated methods," filed Aug. 2, 2024.

Gunning et al.; U.S. Appl. No. 18/847,594 entitled "Thrombus removal systems and associated methods," filed Sep. 16, 2024.

Al-Jadda et al.; U.S. Appl. No. 18/864,484 entitled "Thrombus removal systems and associated methods," filed Nov. 8, 2024.

Saul; U.S. Appl. No. 18/686,616 entitled "Thrombus removal systems and associated methods," filed Nov. 22, 2024.

Saul; U.S. Appl. No. 18/867,656 entitled "Thrombus removal systems and associated methods," filed Nov. 20, 2024.

Dala et al.; U.S. Appl. No. 18/994,012 entitled "Thrombus removal systems and associated methods," filed Jan. 13, 2021.

Al-Jadda et al.; U.S. Appl. No. 19/106,171 entitled "Thrombus removal systems and associated methods," filed Feb. 24, 2025.

Al-Jadda et al.; U.S. Appl. No. 19/106,174 entitled "Contrast injection and visualization systems and methods for thrombus removal device," filed Feb. 24, 2025.

Gunning; U.S. Appl. No. 19/106,179 entitled "Thrombus removal systems and associated methods," filed Feb. 24, 2025.

Srivathsa et al.; U.S. Appl. No. 19/123,721 entitled "Clot visualization and workflows utilizing real-time imaging for thrombus removal systems and methods," filed Apr. 23, 2025.

Al-Jadda et al.; U.S. Appl. No. 19/123,732 entitled "Thrombus removal systems and methods for blood return and reconstituting removed blood clots," filed Apr. 23, 2025.

Gunning et al.; U.S. Appl. No. 19/123,712 entitled "Thrombus removal systems and associated methods," filed Apr. 23, 2025.

Al-Jadda et al.; U.S. Appl. No. 19/123,691 entitled "Thrombectomy system and method of removing thrombus," filed Apr. 23, 2025.

Al-Jadda et al.; U.S. Appl. No. 19/123,734 entitled "Thrombectomy system and method of removing thrombus," filed Apr. 23, 2025.

* cited by examiner

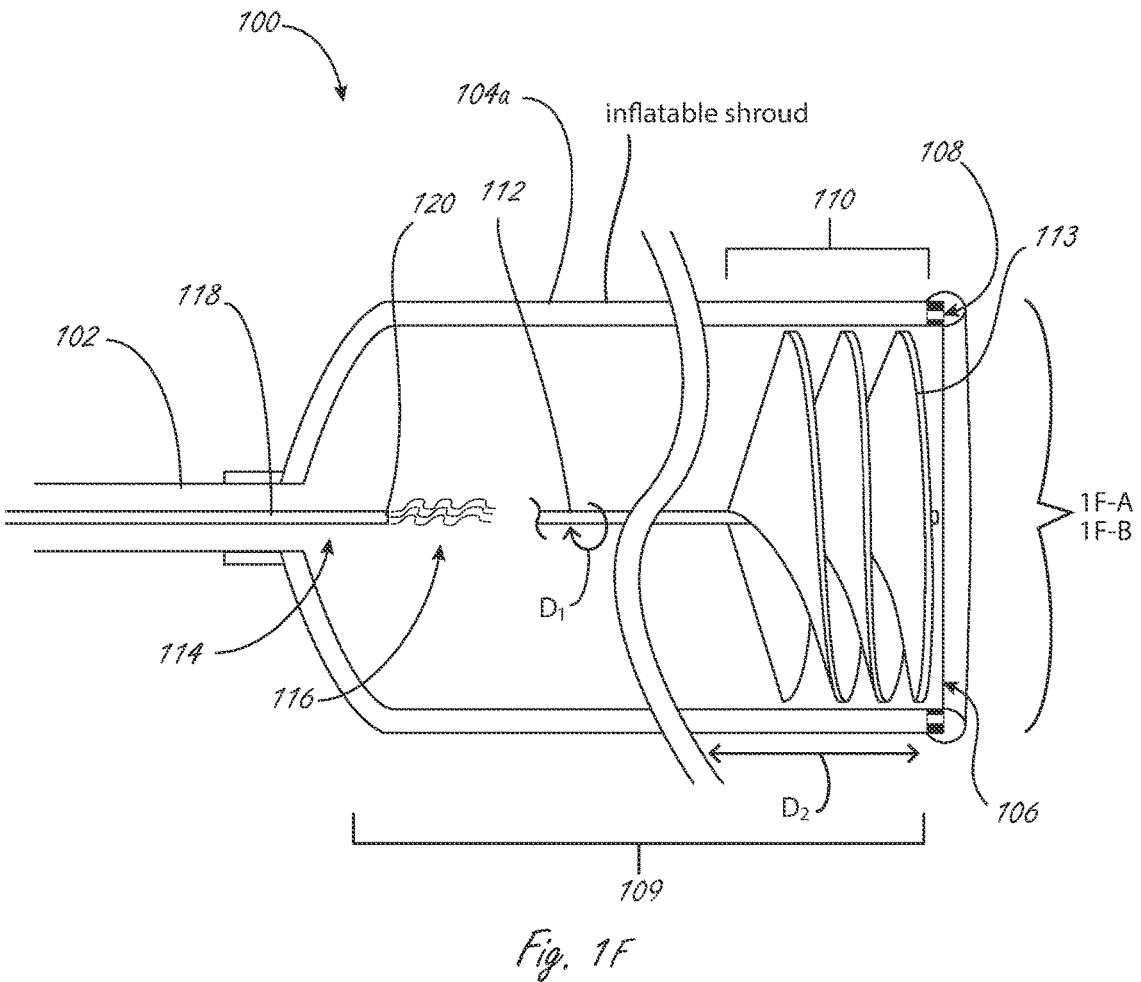
Fig. 1F
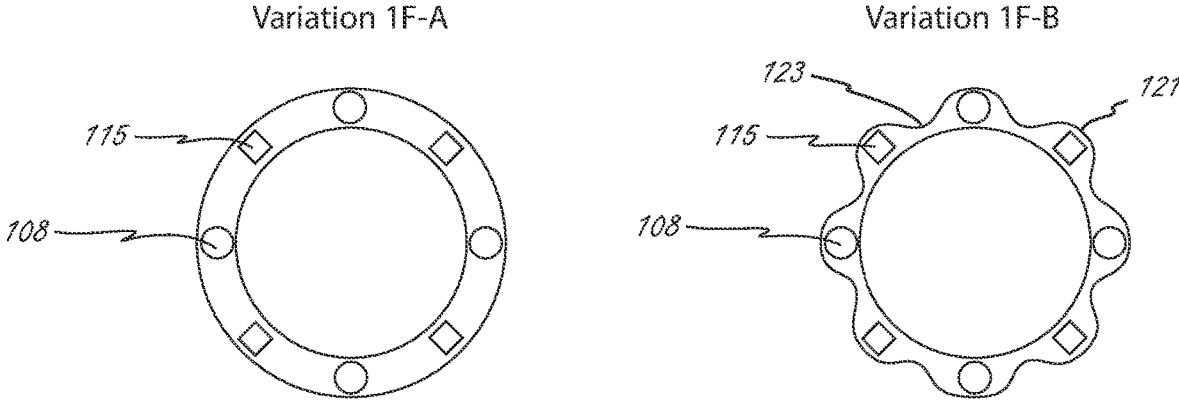
Variation 1F-A                    Variation 1F-B

THROMBUS REMOVAL SYSTEMS AND ASSOCIATED METHODS

CROSS-REFERENCE TO RELATED APPLICATION(S)

This application claims priority to the following applications:

U.S. Provisional Patent Application No. 62/984,918, filed Mar. 4, 2020; and

U.S. Provisional Patent Application No. 63/050,039, filed Jul. 9, 2020.

All of the foregoing applications are incorporated herein by reference in their entireties. Further, components and features disclosed in the applications incorporated by reference may be combined with various components and features disclosed and claimed in the present application.

TECHNICAL FIELD

The present technology generally relates to medical devices and, in particular, to systems and associated methods for removing a thrombus from a patient's blood vessel.

BACKGROUND

A pulmonary embolism is a blockage in one of the pulmonary arteries supplying blood to the lungs. Pulmonary embolisms typically arise when a thrombus originating from another part of the body (e.g., a vein in the pelvis or leg) becomes dislodged and travels to the lungs. Anticoagulation therapy is the current standard of care for treating pulmonary embolisms, but may not be effective in some patients. Additionally, conventional devices for removing thrombotic material may not be capable of navigating the vascular anatomy of the lungs, may not be effective in removing thrombotic material, and/or may lack the ability to provide sensor data or other feedback to the clinician during the thrombectomy procedure.

BRIEF DESCRIPTION OF THE DRAWINGS

FIG. 1D is a side cross-sectional view of the distal portion of FIG. 1C.

FIG. 1F is a side cross-sectional view of a distal portion configured in accordance with other embodiments of the present technology.

FIG. 1G is a side cross-sectional view of a distal portion configured in accordance with another embodiment of the present technology.

DETAILED DESCRIPTION

Figure 1A:
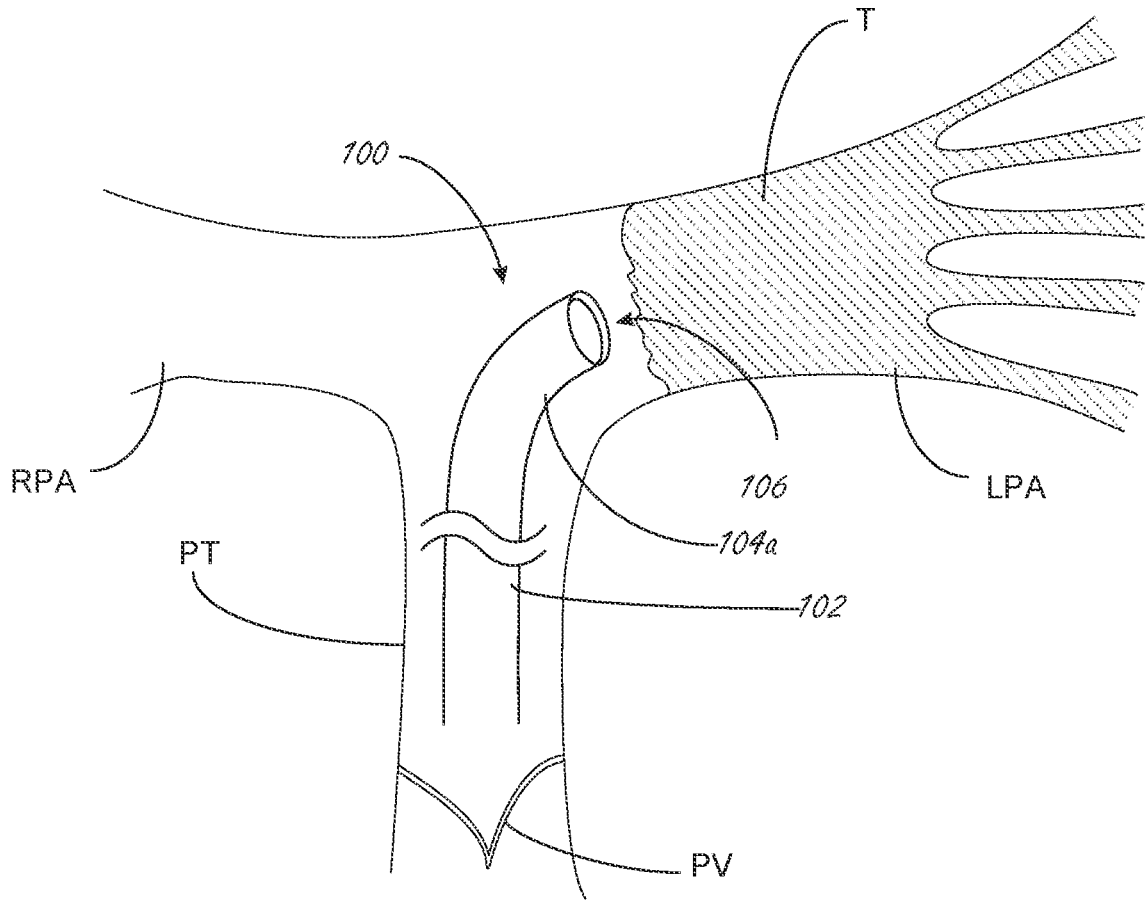
FIG. 1A illustrates a thrombus removal system including an elongated catheter positioned within a patient's pulmonary vasculature and configured in accordance with an embodiment of the present technology.

The present technology is generally directed to thrombus removal systems and associated methods. A system configured in accordance with an embodiment of the present technology can include, for example, an elongated catheter having a distal portion configured to be positioned within the blood vessel of the patient, a proximal portion configured to be external to the patient, and a lumen extending therebetween. The system can also include an imaging element at the distal portion for imaging the patient's vasculature and/or the thrombus. In some embodiments, the system also includes a capture element configured to engage and draw the thrombus into the lumen, a fluid delivery mechanism configured to fragment the thrombus with pressurized fluid, and/or an aspiration mechanism configured to aspirate the fragments of the thrombus.

The terminology used in the description presented below is intended to be interpreted in its broadest reasonable manner, even though it is being used in conjunction with a detailed description of certain specific embodiments of the present technology. Certain terms may even be emphasized below; however, any terminology intended to be interpreted in any restricted manner will be overtly and specifically defined as such in this Detailed Description section. Additionally, the present technology can include other embodiments that are within the scope of the examples but are not described in detail with respect to FIGS. 1A-1G.

Reference throughout this specification to "one embodiment" or "an embodiment" means that a particular feature, structure, or characteristic described in connection with the embodiment is included in at least one embodiment of the present technology. Thus, the appearances of the phrases "in one embodiment" or "in an embodiment" in various places throughout this specification are not necessarily all referring to the same embodiment. Furthermore, the particular features or characteristics may be combined in any suitable manner in one or more embodiments.

Reference throughout this specification to relative terms such as, for example, "generally," "approximately," and "about" are used herein to mean the stated value plus or minus 10%.

Although some embodiments herein are described in terms of thrombus removal, it will be appreciated that the present technology can be used and/or modified to remove other types of emboli that may occlude a blood vessel, such as fat, tissue, or a foreign substance. Additionally, although some embodiments herein are described in the context of thrombus removal from a pulmonary artery (e.g., pulmonary embolectomy), the technology may be applied to removal of thrombi and/or emboli from other portions of the vasculature (e.g., in neurovascular, coronary, or peripheral applications). Moreover, although some embodiments are discussed in terms of maceration of a thrombus with a fluid, the present technology can be adapted for use with other techniques for breaking up a thrombus into smaller fragments or particles (e.g., ultrasonic, mechanical, enzymatic, etc.).

The headings provided herein are for convenience only and do not interpret the scope or meaning of the claimed present technology.

Systems for Thrombus Removal

As provided above, the present technology is generally directed to thrombus removal systems. Such systems include an elongated catheter having a distal portion positionable within a blood vessel of the patient (e.g., an artery or vein), a proximal portion positionable outside the patient's body, and a lumen extending between the distal and proximal portions. In some embodiments, the systems herein are configured to engage a thrombus in the patient's blood vessel, break the thrombus into small fragments, and aspirate the fragments out of the patient's body. Optionally, the systems described herein can include one or more sensors (e.g., a camera) integrated in the elongated catheter (e.g., at the distal portion) to facilitate positioning of the elongated catheter, measure thrombus characteristics, and/or otherwise provide feedback to the clinician during the thrombectomy procedure. As used herein, "thrombus" and "embolism" are used somewhat interchangeably in various respects.

Figure 1B:
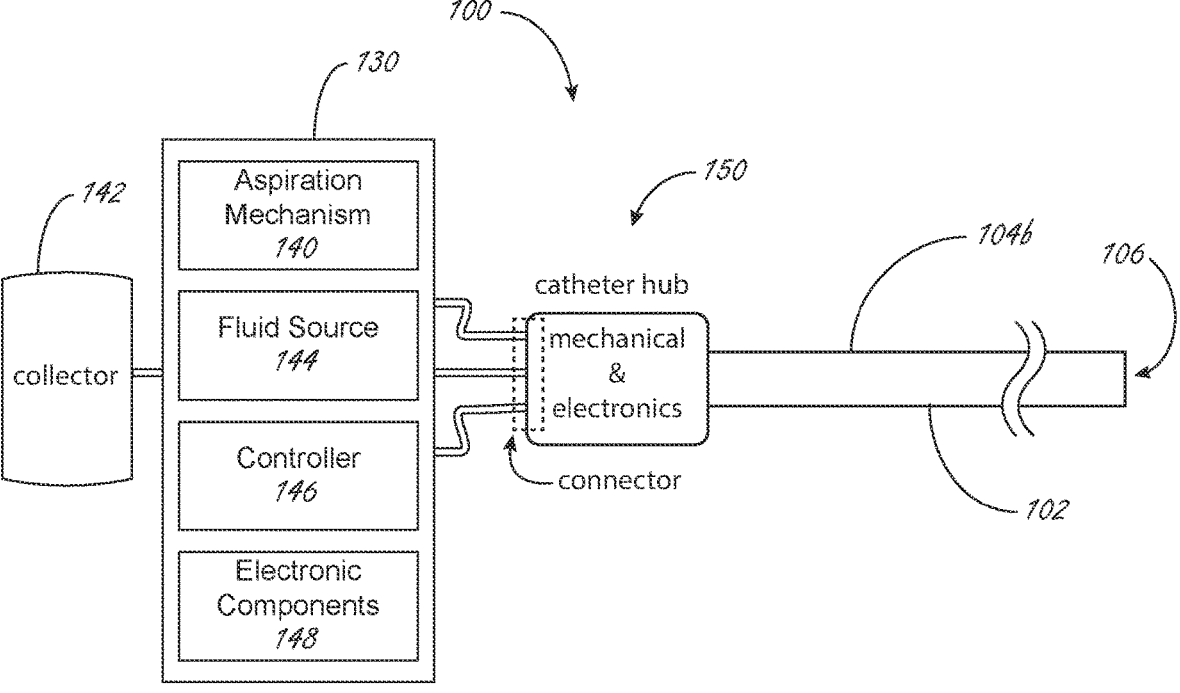
FIG. 1B illustrates a proximal portion of the elongated catheter of FIG. 1A.
Figure 1C:
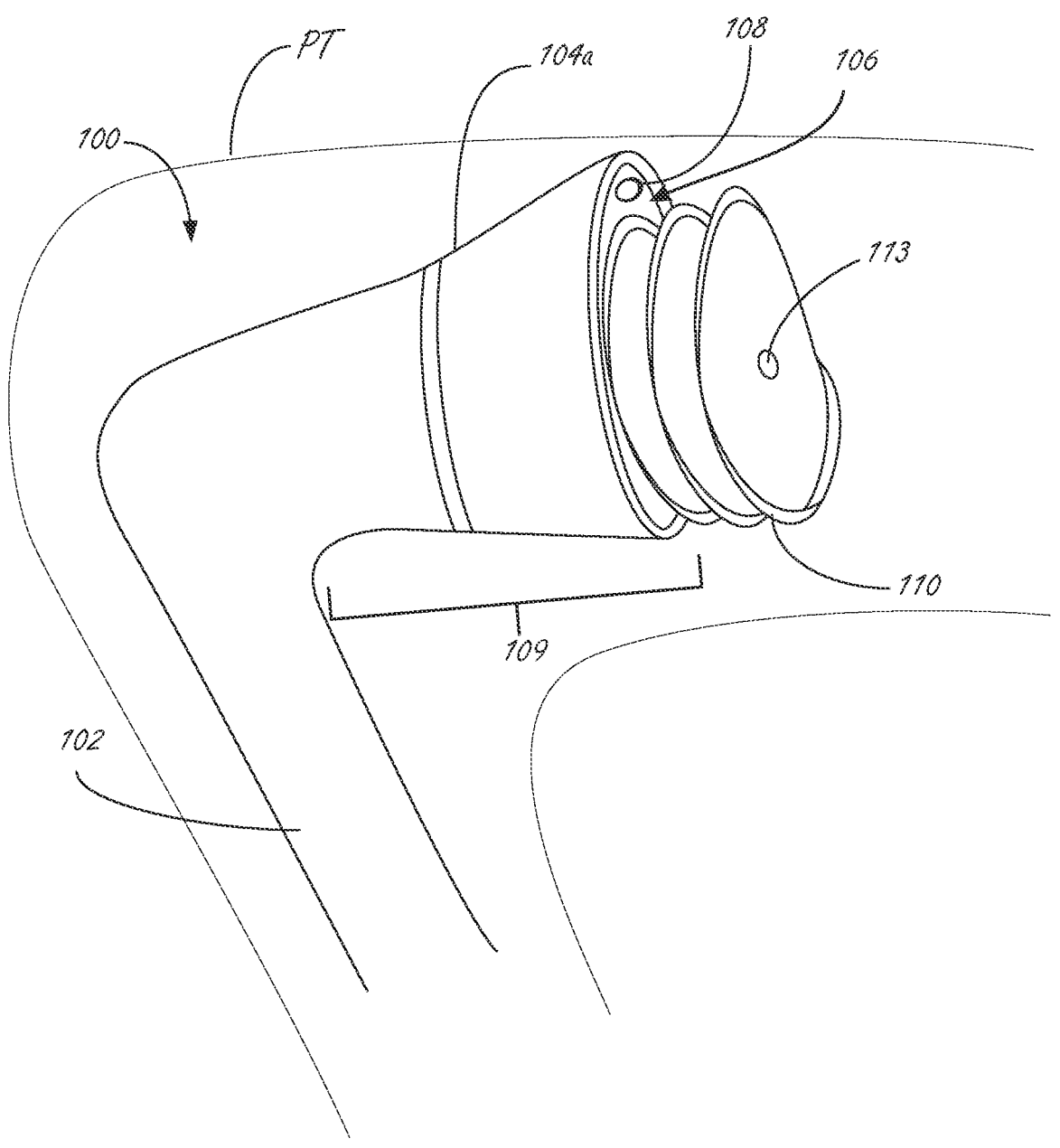
FIG. 1C is a closeup view of a distal portion of the elongated catheter of FIG. 1A.
Figure 10:
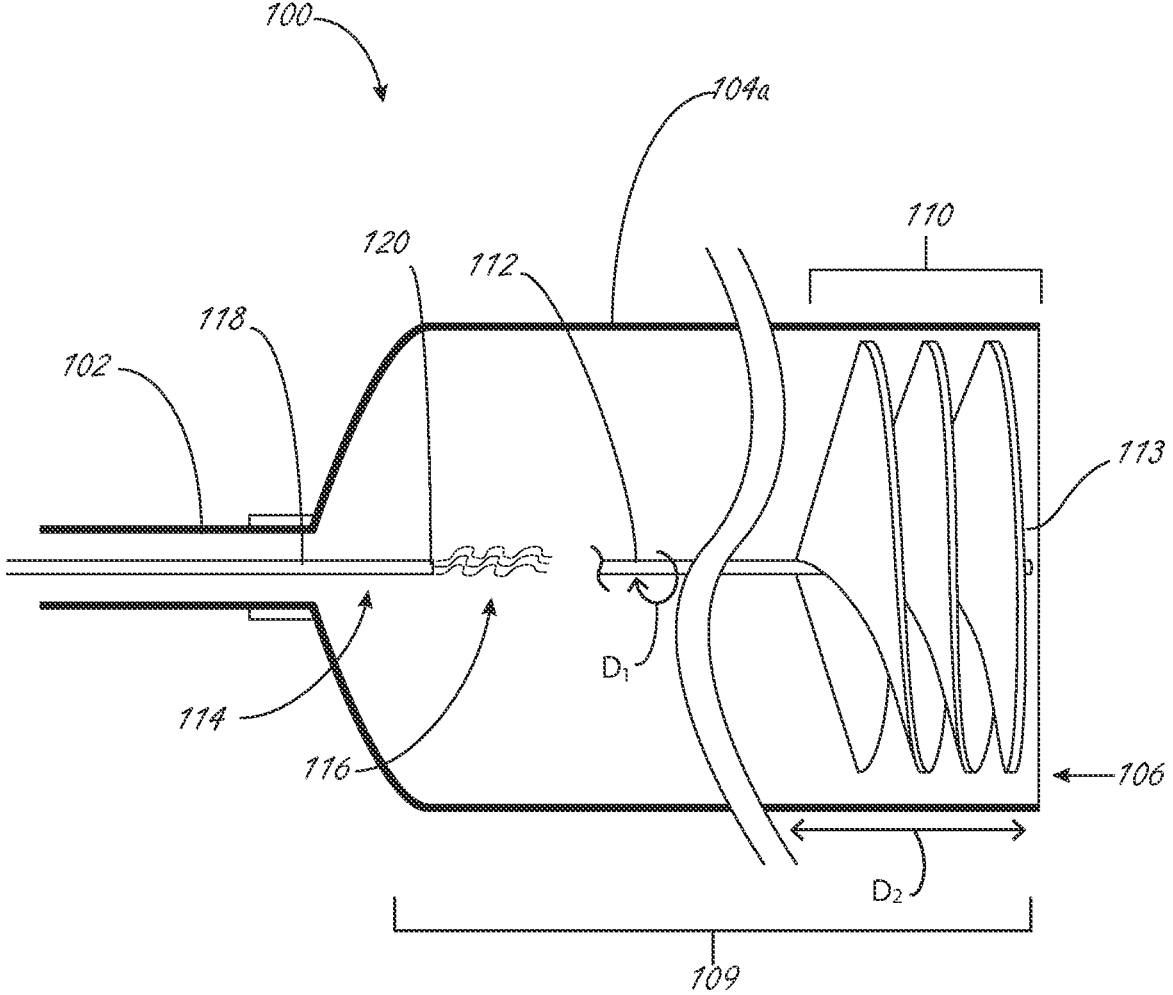
Figure 1E:
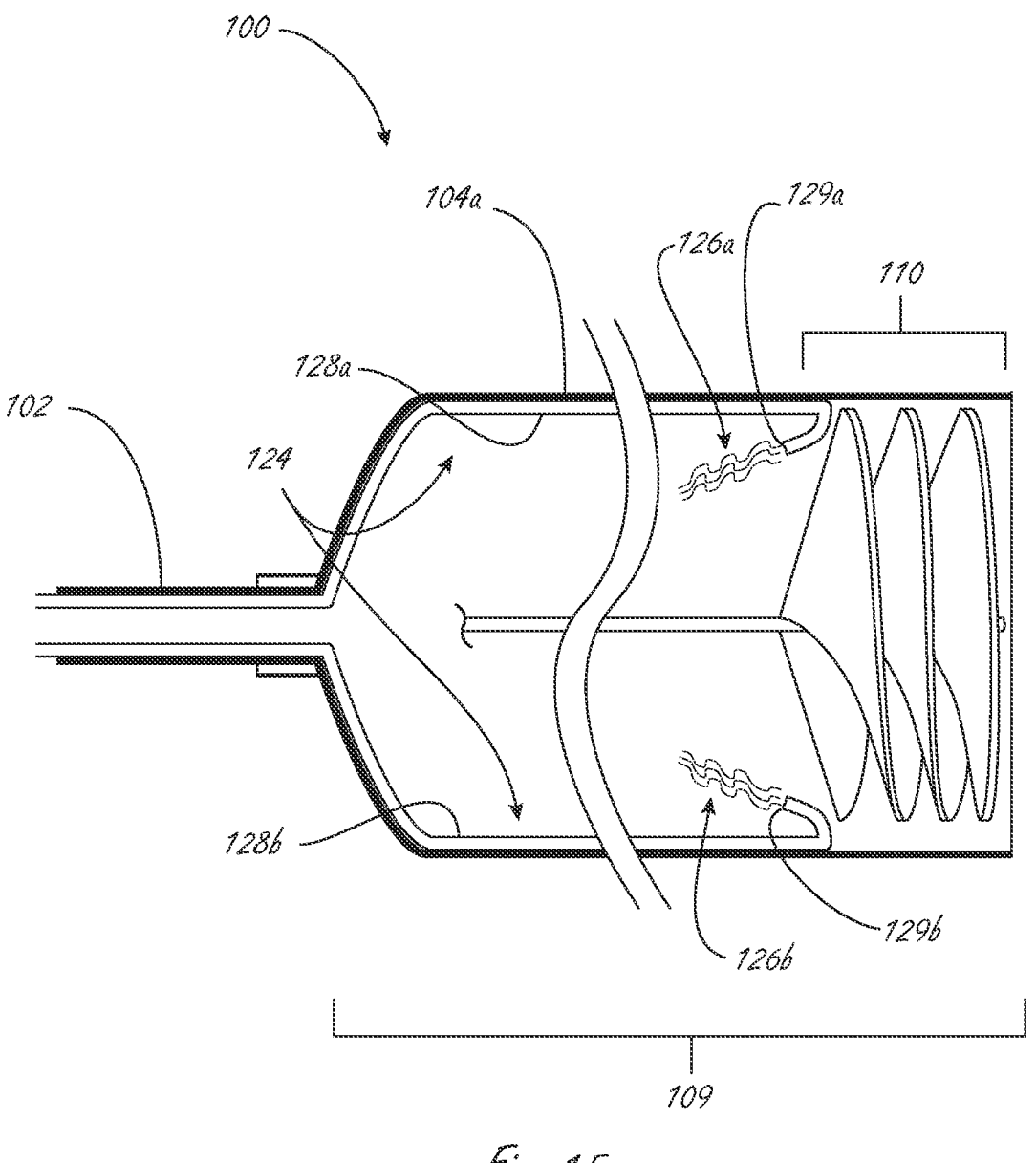
FIG. 1E is a side cross-sectional view of a distal portion configured in accordance with another embodiment of the present technology.
Figure 19:
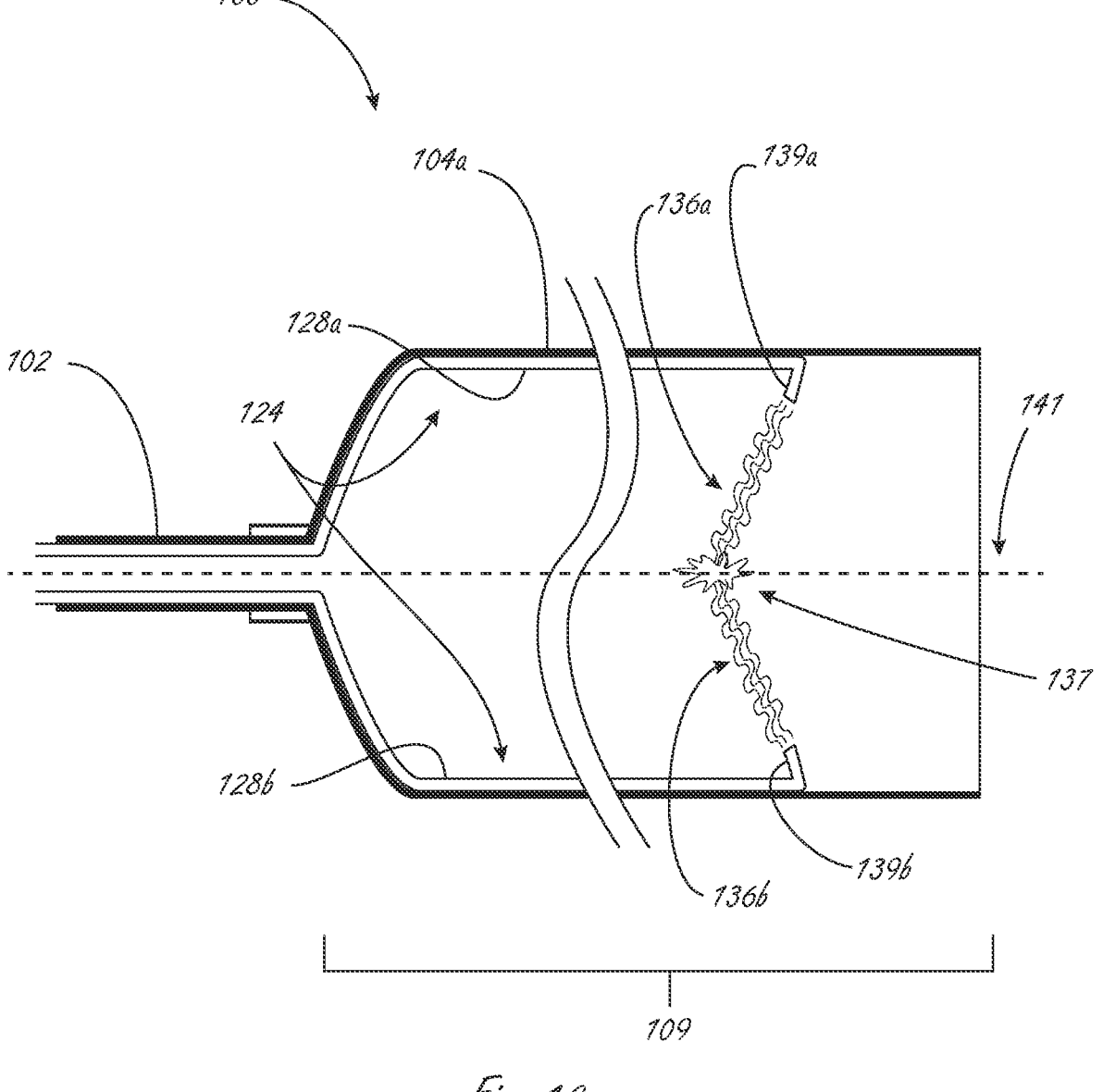

FIGS. 1A-1G illustrate a thrombus removal system 100 configured in accordance with various embodiments of the present technology. More specifically, FIG. 1A illustrates an elongated catheter 102 of the system 100 positioned within a patient's pulmonary vasculature, FIG. 1B illustrates a proximal portion 104*b* of the elongated catheter 102, FIG. 1C is a closeup view of a distal portion 104*a* of the elongated catheter 102, FIG. 1D is a side cross-sectional view of the distal portion 104*a*, FIG. 1E is a side cross-sectional view of some embodiments of the distal portion 104*a*, FIG. 1F is a side cross-sectional view of other embodiments of the distal portion 104*a*, and FIG. 1G is a side cross-sectional view of other embodiments of the distal portion 104*a*.

Referring first to FIG. 1A, the patient's pulmonary vasculature includes a pulmonary valve (PV) separating the right ventricle of the heart (not shown) from the main pulmonary artery or pulmonary trunk (PT). The pulmonary trunk PT splits into the left pulmonary artery (LPA) and the right pulmonary artery (RPA), which connect to the left and right lungs (not shown), respectively. The diameter of the pulmonary trunk PT can vary significantly, e.g., between about 22 mm to about 43 mm during systole and diastole. The left pulmonary artery LPA and right pulmonary artery RPA can each have a diameter within a range from 16 mm to 49 mm, and a length within a range from about 80 mm to about 100 mm. A pulmonary embolism occurs when one or more portions of the pulmonary vasculature are occluded by a thrombus T. For example, in the illustrated embodiment, the thrombus (T) is blocking the left pulmonary artery (LPA).

Referring to FIGS. 1A and 1B together, the thrombus removal system 100 can be used to remove the thrombus T from the patient's vasculature. The elongated catheter 102 of the system 100 includes a lumen 106 extending therethrough between distal and proximal portions 104*a*-*b*. The distal portion 104*a* is configured to be positioned within a blood vessel at a location near or adjacent to the thrombus T. The elongated catheter 102 or at least a portion thereof (e.g., the distal portion 104*a*) can be introduced into the patient's body (e.g., via a delivery sheath—not shown) and advanced to the site of the thrombus T. For example, in the illustrated embodiment, the elongated catheter 102 is advanced through the pulmonary valve PV into the pulmonary trunk PT and at least partially into the left pulmonary artery LPA or right pulmonary artery RPA so that distal portion 104*a* is adjacent to the thrombus T. The proximal portion 104*b* is configured to remain external to the patient's body, as described in greater detail below. The proximal portion 104*b* can include or be coupled to a handle (not shown) for controlling movement and/or other functions of the elongated catheter 102. Although described in relation to a procedure in the pulmonary artery, one will appreciate from the description herein that the systems, devices, and methods described may be applied equally to other locations in the body and other diseases. For example, the systems and devices may be used to remove thrombus from any type of occluded arteries, veins, or prostheses (e.g. vascular grafts). The systems, devices, and methods may be used as adjunctive therapy or as a sole therapy. In various embodiments, the system is configured to remove pulmonary emboli, iliofemoral emboli, and/or deep venous thromboses.

In some embodiments, the elongated catheter 102 or a portion thereof (e.g., the distal portion 104*a*, an intermediate portion between the distal and proximal portions 104*a*-*b*—not shown) has a relatively small outer diameter suitable for introduction into the patient's vasculature (e.g., the pulmonary vasculature). The outer diameter can be smaller than the diameter of the target blood vessel so that the elongated catheter 102 does not completely occlude the blood vessel when introduced therein. For example, the outer diameter can be less than or equal to about 10 mm, less than or equal to about 9 mm, less than or equal to about 8 mm, less than or equal to about 7.5 mm, less than or equal to about 7 mm, less than or equal to about 6.5 mm, less than or equal to about 6 mm, less than or equal to about 5.5 mm, less than or equal to about 5 mm, less than or equal to about 4.5 mm, less than or equal to about 4 mm, less than or equal to about 3.5 mm, less than or equal to about 3 mm, less than or equal to about 2.5 mm, less than or equal to about 2 mm, less than or equal to about 1.5 mm, or less than or equal to about 1 mm. In some embodiments, the outer diameter is less than or equal to 21 French (Fr), less than or equal to 10 Fr, or within a range from about 10 Fr to about 4 Fr. The distal portion 104*a* of the elongated catheter 102 can be configured to facilitate navigation through the patient's vasculature. For example, the catheter can be steerable. The catheter may be relatively flexible to be guided over a guidewire or have a tip configured to be pushed through the vasculature. Optionally, the elongated catheter 102 or a portion thereof can have sufficient stiffness to reduce or prevent kinking, pinching, etc. as the elongated catheter 102 is introduced through bends, curves, branches, or other tortuous portions of the vascular anatomy.

Referring to FIG. 1C, in some embodiments the distal portion 104*a* of the elongated catheter 102 includes an imaging element 108 (e.g., a camera, such as CCD camera, or CMOS camera). The imaging element 108 can be operably coupled to an exterior surface of the distal portion 104*a*, operably coupled to an interior surface of the distal portion 104*a* (e.g., within the lumen 106), or can be embedded within a wall of the distal portion 104*a* around the lumen 106. The imaging element 108 can be configured to generate an image and/or data representative of the patient's vasculature and/or the thrombus (not shown in FIG. 1C) to guide the clinician in performing the thrombectomy procedure. For example, image data can be displayed to assist the clinician in positioning the distal portion 104*a* near the thrombus. The image data can also help the clinician assess the type of thrombus (e.g., soft and acute, slightly organized with some fibrin, highly organized and fibrotic, etc.) to determine the appropriate procedure and/or tools for removing the thrombus. Optionally, the imaging element 108 can generate image data before, during, and/or after the thrombectomy procedure so the clinician can evaluate whether the thrombus has been completely removed, whether there are any portions or other thrombi remaining in the blood vessel, whether other treatment procedures would be beneficial, etc.

The system 100 can include additional components configured to facilitate visualization of the treatment site with the imaging element 108. For example, the system 100 can include an illumination source (e.g., one or more LEDS—not shown) at or near the distal portion 104*a*. The system 100 can also be configured to deliver a fluid (e.g., a fluid that is transparent in the visible spectrum) to provide an optical path to the location of interest. The fluid can be delivered from the distal portion 104*a* to displace opaque blood away from the treatment site and provide an optically transparent medium for imaging. In some embodiments, the fluid for imaging is the same as the fluid used to fragment the thrombus, as described further below. In other embodiments the fluid for imaging is different from the fluid for fragmenting the thrombus.

Referring to FIGS. 1C and 1D together, in some embodiments the distal portion 104a of the elongated catheter 102 includes an expandable chamber 109. The interior space within the expandable chamber 109 can be part of or be connected to the lumen 106 so that materials can enter and/or exit the elongated catheter 102 via the expandable chamber 109. The expandable chamber 109 can be transformed between a deployed configuration (e.g., an expanded and/or generally cylindrical configuration as shown in FIGS. 1C and 1D) and a low-profile configuration (e.g., a collapsed, contracted and/or flattened configuration—not shown). The expandable chamber 109 can assume the low-profile configuration to allow the distal portion 104a of the elongated catheter 102 to be intravascularly introduced into the patient's body via a delivery sheath or other minimally invasive techniques. Once the distal portion 104a is positioned at the target site within the blood vessel, the expandable chamber 109 can be transformed into the deployed configuration for capturing and macerating the thrombus, as described in greater detail below. The expandable chamber 109 can be self-expanding so that it automatically transforms into the deployed configuration when released from the delivery sheath. Subsequently, when the thrombectomy procedure is completed, the expandable chamber 109 can be transformed back into the low-profile configuration and withdrawn into the delivery sheath for removal from the patient's body. Alternatively or additionally, the expandable chamber 109 can be inflatable (e.g., by a fluid or a gas) to transform from the low-profile configuration to the deployed configuration.

The geometry (e.g., size, shape) of the expandable chamber 109 can be configured in a number of different ways. For example, the expandable chamber 109 can have a circular, elliptical, square, rectangular, polygonal, curvilinear, star, or other cross-sectional shape. In some embodiments, the expandable chamber 109 has a uniform cross-sectional shape throughout its entire length (e.g., the expandable chamber 109 is a generally cylindrical structure), while in other embodiments the expandable chamber 109 has a variable cross-sectional shape (e.g., the expandable chamber 109 is a funnel-like structure). The expandable chamber 109 can have a length at least about 5 cm, at least about 6 cm, at least about 7 cm, at least about 7.5 cm, at least about 8 cm, at least about 8.5 cm, at least about 9 cm, at least about 9.5 cm, at least about 10 cm, at least about 10.5 cm, at least about 11 cm, or at least about 12 cm. In some embodiments, the length of the expandable chamber 109 is within a range from about 8 cm to about 10 cm. When in the deployed configuration, the expandable chamber 109 can have an outer diameter at least about 5 mm, at least about 5.5 mm, at least about 6 mm, at least about 6.5 mm, at least about 7 mm, at least about 7.5 mm, at least about 8 mm, at least about 8.5 mm, at least about 9 mm, at least about 9.5 mm, at least about 10 mm, at least about 15 mm, at least about 20 mm, at least about 25 mm, at least about 30 mm, at least about 35 mm, or at least about 40 mm. When in the low-profile configuration, the expandable chamber 109 can have an outer diameter at most about 7 mm, at most about 6.5 mm, at most about 6 mm, at most about 5.5 mm, at most about 5 mm, at most about 4.5 mm, at most about 4 mm, at most about 3.5 mm, at most about 3 mm, at most about 2.5 mm, at most about 2 mm, at most about 1.5 mm, or at most about 1 mm. The cross-sectional dimension (e.g., area, diameter, width, etc.) of the expandable chamber 109 in the deployed configuration can be at least about 50%, at least about 60%, at least about 70%, at least about 80%, at least about 90%, at least about 100%, at least about 150%, at least about 200%, at least about 250%, at least about 300%, at least about 400%, at least about 500%, at least about 600%, at least about 700%, at least about 800%, at least about 900%, or at least about 1000% greater than the cross-sectional dimension of the expandable chamber 109 in the low-profile configuration. In some embodiments, when in the deployed configuration, the cross-sectional dimension of the expandable chamber 109 is at least about 50%, at least about 60%, at least about 70%, at least about 80%, at least about 90%, at least about 100%, at least about 150%, at least about 200%, at least about 250%, at least about 300%, at least about 400%, or at least about 500% greater than a cross-sectional dimension of a remaining portion of the elongated catheter 102 (e.g., the intermediate portion between the distal and proximal portions 104a-b).

Optionally, when in the deployed configuration, the cross-sectional dimension of the expandable chamber 109 can be less than the cross-sectional dimension of the blood vessel in which the expandable chamber 109 is positioned. For example, the diameter of the expandable chamber 109 can be about 10%, about 20%, about 30%, about 40%, about 50%, about 60%, about 70%, about 80%, or about 90% of the diameter (e.g., minimum or maximum diameter) of the blood vessel. In some embodiments, when deployed, the expandable chamber 109 is configured to engage and form a seal against the thrombus while permitting blood flow around the exterior of the expandable chamber 109 and/or thrombus to maintain perfusion. The sealing of the expandable chamber 109 against the thrombus can allow fluid (e.g., for imaging and/or fragmenting thrombus) to be delivered, contained, and aspirated from the expandable chamber 109 with little or no leakage into the patient's bloodstream, as described further below.

Alternatively, when in the deployed configuration, the cross-sectional dimension of the expandable chamber 109 can be equal or approximately equal to the cross-sectional dimension of the blood vessel such that the expandable chamber 109 partially or completely occludes fluid flow therethrough. For example, the expandable chamber 109 in the deployed configuration can form a fluid seal about a perimeter of the expandable chamber 109, against the wall of the blood vessel. The seal may a partial fluid seal or complete fluid seal (clinically and/or functionally complete seal). This approach is designed to prevent thrombus fragments from traveling to other parts of the patient's body during the thrombectomy procedure, and can be utilized in situations where tissues downstream of the expandable chamber 109 are still perfused by other blood vessels and/or where temporary upstream occlusion by the expandable chamber 109 can be tolerated. In some embodiments, the expandable chamber 109 can include one or more valves (not shown) configured to selectively permit fluid flow along an exterior of the system 100. For example, the one or more valves can be located about the perimeter of the expandable chamber 109. This approach can be advantageous in situations where tissue perfusion downstream of the expandable chamber 109 may be compromised in the case of a total or near-total occlusion by the expandable chamber 109.

The expandable chamber 109 can be used to house one or more components of the system 100. In some embodiments, for example, the system 100 includes a capture element 110 at the distal portion 104a and at least partially within the expandable chamber 109. The capture element 110 can be configured to contact and engage the thrombus to draw the thrombus at least partially into the lumen 106 and the expandable chamber 109. Various types of capture elements are suitable for use with the embodiments described herein. For example, as best seen in FIG. 1D, the capture element 110 can be configured as an auger, screw (e.g., an Archimedes screw), or other helical structure that is configured to rotate (e.g., along direction D1) to penetrate into the thrombus and/or progressively draw the thrombus into the lumen 106. The geometry (e.g., size, shape) of the capture element 110 can be configured in a number of different ways. In some embodiments, the capture element is formed to have an outer perimeter (e.g., profile) that is generally uniform along its axial length (e.g., along direction D2). In some embodiments, the capture element 110 has a variable profile. For example, the capture element 110 can have a conical profile that is tapered in the distal direction and/or in the proximal direction. Alternatively or in combination with rotation, the capture element 110 can be movable in a longitudinal direction (e.g., direction D2) to engage and progressively draw the thrombus into the lumen 106 and the expandable chamber 109. In some embodiments, the capture element 110 is movable along a distance that is at least about 10%, at least about 20%, at least about 30%, at least about 40%, at least about 50%, at least about 60%, at least about 70%, at least about 80%, at least about 90%, or at least about 100% of the length of the capture element 110. Longitudinal movement of the capture element 110 (e.g., out of the lumen 106 and the expandable chamber 109) can also be used to clear the capture element 110 if it becomes jammed or clogged.

The rotational and/or longitudinal movement of the capture element 110 relative to the distal portion 104*a* can be actuated by a drive shaft 112 extending through the elongated catheter 102 and into the expandable chamber 109. The drive shaft 112 can operably couple the capture element 110 to a motor, cam, and/or other actuation mechanism at the proximal portion of the elongated catheter 102 (not shown). In some embodiments, the rotation speed of the capture element 110 is adjustable (e.g., between high, medium, and low speeds) to facilitate engagement with different thrombus types. For example, slower rotation speeds can be used to capture softer, less organized, and/or less fibrotic thrombi, while faster rotation speeds can be used to capture harder, more organized, and/or more fibrotic thrombi.

Optionally, the properties of the capture element 110 (e.g., thread size, thread pitch, and/or durometer) can be selected based on the type and/or the characteristics of the thrombus (e.g., stiffness, density, degree of organization, fibrin content, size, etc.). In some embodiments, the capture element 110 includes at least one sensor 113 (e.g., located at a distal portion of the capture element 110) for sensing one or more characteristics of the thrombus. For example, the sensor 113 can be configured to measure strain, stiffness, and/or other mechanical properties of the thrombus. As another example, the sensor 113 can be configured to measure current, impedance, and/or other electrical properties of the thrombus (e.g., while the capture element 110 is rotating). Other types of sensors suitable for use with the embodiments herein include pressure sensors, accelerometers, temperature sensors, flow sensors, optical sensors, microphones or other acoustic sensors, ultrasonic sensors, ECG or other cardiac rhythm sensors, SpO2 sensors, electrical impedance sensors, and other sensors adapted to measure tissue and/or blood gas levels, blood volume sensors, and other sensors known to those who are skilled in the art. The sensor data generated by the sensor 113 can be transmitted to an external computing device via wired or wireless communication so that the sensor data can be processed and/or displayed to the clinician.

In some embodiments, the capture element 110 is expandable (e.g., inflatable) and can be transformed between a low-profile configuration (e.g., a flattened and/or collapsed configuration—not shown) and a deployed configuration (e.g., an operating and/or expanded configuration for engaging a thrombus, as shown in FIGS. 1C and 1D). The capture element 110 can be transformed into the low-profile configuration while the expandable chamber 109 is also in the low-profile configuration, e.g., for introduction into the patient's blood vessel. Once the distal portion 104*a* is properly positioned within the blood vessel, the capture element 110 can be transformed into the deployed configuration, e.g., concurrently with or after transformation of the expandable chamber 109 into the deployed configuration. In some embodiments, a portion or an entirety of the capture element 110 is inflatable using delivered fluid and/or gas. A portion can comprise a). one or more blades (e.g., of an impeller), or b). one or more blade portions (e.g., peripheral edge of a given blade). In some embodiments, the body of the capture element comprises a membrane that includes an outer portion (e.g., edge) that is inflatable. In some embodiments, the capture element 110 is configured to be self-expanding so that it automatically transforms along with the expandable chamber 109 into the deployed configuration when unsheathed and/or unrestrained. The capture element 110 can then be used to engage and draw a thrombus into the expandable chamber 109, as described herein. The capture element 110 can be transformed back into the low-profile configuration, e.g., after the thrombus has been collected and/or along with transformation of the expandable chamber 109 into the low-profile configuration.

Referring to FIG. 1D, the system 100 can also include a fluid delivery mechanism 114 at the distal portion 104*a* and at least partially within the expandable chamber 109. The fluid delivery mechanism 114 can be configured to apply a fluid 116 (e.g., saline) to fragment, macerate, cut, pulverize, and/or otherwise break up the thrombus into a plurality of smaller particles. For example, the delivery mechanism 114 can be positioned proximal to the capture element 110 so that as a section of the thrombus is drawn proximally into the expandable chamber 109 by the capture element 110, the fluid delivery mechanism 114 fragments the section of the thrombus with the fluid 116. In some embodiments, the fluid 116 is pressurized to contact the thrombus with sufficient force to fragment the thrombus. The fluid 116 can be delivered in a continuous stream or jet, or can be delivered intermittently at a specified timing, frequency, etc. The pressure and/or flow rate of the fluid 116 can be sufficiently large to break up the thrombus, but sufficiently small so that little or no fluid 116 escapes from the lumen 106 and into the patient's blood stream. In some embodiments, the applied fluid 116 is delivered proximal to a seal that is formed by the expandable chamber 109. Advantageously, applied fluid 116 that is delivered proximal to a seal is expected to improve the efficacy and/or efficiency of a) maceration/fragmentation of the thrombus, and/or b) aspiration of thrombus fragments. Optionally, the pressure and/or flow rate can be selectively adjusted based on the type and/or characteristics of the thrombus (e.g., a higher pressure and/or flow rate for harder, more organized, and/or more fibrotic thrombi; a lower pressure and/or flow rate for softer, less organized, and/or less fibrotic thrombi). In some embodiments, the applied fluid 116 is delivered at a pressure that is at least about 50 pounds per square inch (psi), at least about 70 psi, at least about 90 psi, at least about 110 psi, at least about 130 psi, or at least about 150 psi. In some embodiments, the applied fluid 116 can be delivered at a pressure from at least about 50 psi to at least about 1000 psi—for example, at least about 50 psi, at least about 100 psi, at least about 200 psi, at least about 300 psi, at least about 400 psi, at least about 500 psi, at least about 600 psi, at least about 700 psi, at least about 800 psi, at least about 900 psi, or at least about 1000 psi. The applied fluid 116 can be delivered at any pressure within the aforementioned ranges of pressures. In some embodiments, the applied fluid 116 is delivered for a given duration, for example, at least about 100 milliseconds (ms), at least about 200 ms, at least about 300 ms, at least about 400 ms, at least about 500 ms, at least about 600 ms, at least about 700 ms, at least about 800 ms, at least about 900 ms, or at least about 1 second. The applied fluid 116 can be delivered for any duration within the aforementioned range of durations. In some embodiments, the applied fluid 116 is delivered intermittently and/or periodically (e.g., in pulses), for a given duration. Advantageously, pulsing the applied fluid 116 can reduce a total volume of fluid that delivered to patient. For example, the applied fluid 116 can be delivered periodically with an (application) frequency of about 0.1 hertz (Hz), about 0.3 Hz, about 0.5 Hz, about 0.7 Hz, about 1 Hz, about 2 Hz, about 3 Hz, about 4 Hz, or about 5 Hz. The delivery of the applied fluid 116 can be at any frequency within the aforementioned range of frequencies. In some embodiments, a frequency with which the applied fluid 116 is delivered may be varied—for example, varied before, during, and/or after application of a given pulse of delivered fluid.

The fluid delivery mechanism 114 can be configured in a number of different ways. In the illustrated embodiment, for example, the fluid delivery mechanism 114 includes a single elongated tube 118 terminating in an opening 120 (e.g., a fluid port or nozzle). The opening 120 can be positioned within the expandable chamber 109 proximal to and spaced apart from the capture element 110 so that a thrombus or section thereof can be received within the expandable chamber 109 between the opening 120 and the capture element 110. The elongated tube 118 and opening 120 are oriented along the longitudinal axis of the distal portion 104a such that fluid 116 is directed distally toward the capture element 110. Accordingly, when a thrombus is drawn proximally into the expandable chamber 109 by the capture element 110, the fluid 116 is applied distally against the thrombus to fragment the thrombus.

Referring to FIG. 1E, in other embodiments the system 100 can include a fluid delivery mechanism 124 configured to produce two or more fluid jets or streams (e.g., two fluid jets 126a-b). The fluid delivery mechanism 124 can include two elongated tubes 128a-b each terminating in a respective opening 129a-b. The elongated tubes 128a-b can extend along opposite interior surfaces of the expandable chamber 109 with the openings 129a-b located adjacent to or near the proximal portion of the capture element 110. The openings 129a-b and/or the distal portions of the elongated tubes 128a-b can be oriented proximally toward the central longitudinal axis of the expandable chamber 109. As a result, the fluid jets 126a-b are directed proximally away from the capture element 110 and toward the center of the expandable chamber 109. When a thrombus is drawn proximally into the expandable chamber 109 by the capture element 110, the fluid jets 126a-b are applied proximally against the thrombus to fragment the thrombus.

It will be appreciated that the system 100 can include fluid delivery mechanisms that differ from the embodiments shown in FIGS. 1D, 1E and 1G. For example, a fluid delivery mechanism can include any suitable number of elongated tubes or like structures for transporting fluid (e.g., one, two, three, four, five, ten, twenty, thirty or more elongated tubes). The fluid delivery mechanism can include any number of structures within the aforementioned ranges. Each elongated tube can include one or more openings (e.g., one, two, three, four, five, or more openings) for delivering fluid therethrough. In some embodiments, a single elongated tube includes a plurality of openings at different locations along the length of the tube so as to apply fluid to different portions of a captured thrombus. The fluid can be directed proximally, distally, toward a central longitudinal axis (e.g., FIG. 1G, 141), combinations of the foregoing, or in any other direction suitable for fragmenting the thrombus. In some embodiments, openings are arranged to direct the fluid streams generally along an inner wall of the distal portion 104a.

In some embodiments a pressure with which the fluid is delivered in a given stream is selected such that the stream dissipates prior to impacting an inner wall of the distal portion 104a. For example, the pressure may be sufficiently low such that, for an opening that directs a fluid stream from a first wall portion in a path toward a second wall portion, the fluid stream will dissipate prior to impacting the second wall portion. In some embodiments, the second wall portion is opposite the first wall portion. Dissipation may comprise a loss of cohesion for a fluid stream, a reduction in fluid stream momentum, or a change in fluid stream momentum (e.g., toward a proximal direction). Dissipation of a fluid stream may comprise a reduction in a magnitude of at most about 60%, at most about 50%, at most about 40%, at most about 30%, at most about 20%, at most about 10%, at most about 5%, or at most about 1% of the (e.g., initial) momentum with which the fluid stream was delivered to its given opening. The reduction in momentum can be any reduction within the aforementioned range of reduced momentums. Optionally, in some embodiments some or all of the elongated tubes can be used to deliver fluid to create a transparent optical path for imaging, e.g., in addition or alternatively to delivering fluid for breaking up the thrombus.

Referring to FIGS. 1B and 1D together, the system 100 also includes an aspiration mechanism 140 (best seen in FIG. 1B-shown schematically) fluidly coupled to the lumen 106. The aspiration mechanism 140 can be an active aspiration mechanism or a passive aspiration mechanism, and can include any device suitable for generating a vacuum (e.g., a vacuum pump). In operation, the aspiration mechanism is placed (e.g., via lumen 106) in fluid communication with the distal portion 104a. The aspiration mechanism 140 can be configured to aspirate the fragmented thrombus from the distal portion 104a of the elongated catheter 102 (e.g., from the expandable chamber 109) to the proximal portion 104b, and optionally to a collection container 142. In some embodiments, the aspiration mechanism 140 can be configured to supplement and/or replace the capture element 110 to draw the thrombus into the lumen 106 (best seen in FIG. 1G). For example, the aspiration mechanism 140 can be activated when the distal portion 104a is near and/or in contact with the thrombus, to reduce (e.g., lower) pressure within the distal portion 104a. For example, the aspiration mechanism 140 can be a Venturi vacuum pump in which a pump fluid (e.g., water) is passed through the pump to create a vacuum in a side port, as is known to those of skill in the art. The pump fluid and aspirated materials can be collected in the container 142. Optionally, collected fluids can be filtered and reused to continue running the pump.

The amount of vacuum pressure applied by the aspiration mechanism 140 can be selected (e.g., sufficiently high) to effectively aspirate the thrombus through the length of the elongated catheter 102. The vacuum pressure can also be selected (e.g., sufficiently high) so that most or all of the fluid 116 produced by the fluid delivery mechanism (e.g., fluid delivery mechanism 114 of FIG. 1D or fluid delivery mechanism 124 of FIG. 1E) is aspirated and does not accumulate in the patient's blood stream. However, the vacuum pressure can also be selected (e.g., sufficiently low) so that the aspiration mechanism 140 aspirates little or no blood out of the patient's body. In some embodiments, the system 100 includes one or more sensors (e.g., pressure sensors, flow sensors, etc.—not shown) configured to monitor fluid flow, volume, and/or pressure of fluids moving into and/or out of the patient's blood stream. Based on the sensor data, the operating parameters of the fluid delivery mechanism (e.g., fluid delivery mechanism 114 of FIG. 1D or fluid delivery mechanism 124 of FIG. 1E) and/or aspiration mechanism 140 can be adjusted to regulate the amount of fluid flow into and/or out of the patient's blood stream.

In some embodiments, the system 100 includes an expandable housing. The expandable housing can comprise, for example, an expandable scaffold or frame, an inflatable shroud, or a balloon. In some embodiments, the system 100 includes a plurality of imaging elements and/or a plurality of illumination elements. In some embodiments, one or more imaging elements and/or illumination elements are housed in the expandable housing. The expandable housing can be at least partially transparent to light generated by the illumination elements and/or detected by the imaging element. The inflatable shroud can be positioned at a distal portion of the elongated catheter (e.g., 104a). In some embodiments the inflatable shroud at least partially (e.g., completely) encompasses the chamber 109. The inflatable shroud can be expandable by ingress of fluid or gas. For example, the inflatable shroud can be expanded by saline, oil, $CO_2$, and/or a substantially inert gas. In some embodiments, the aspiration fluid and the fluid filling the inflatable shroud are the same. In some embodiments, the inflatable shroud is reversibly adjustable from a collapsed first configuration to an expanded second configuration. In some embodiments, the inflatable shroud can be collapsed in an axially-variable manner, wherein a first axial portion of the inflatable shroud is collapsed at a different time than a second axial portion of the inflatable shroud. For example, the inflatable shroud may be collapsed in a distal-to-proximal manner (e.g., is distally collapsible). In some embodiments, the inflatable shroud can be collapsed in a proximal-to-distal manner. Advantageously, collapsing the inflatable shroud in an axially-variable can assist in a) fragmentation of the thrombus, and/or b) proximal motivation of the thrombus and/or of thrombus fragments. In some embodiments, fluid delivery openings (e.g., 129a-b) that are carried by an inflatable shroud may be directed (e.g., targeted) by inflation of the inflatable shroud to transform to a selected geometry and/or configuration. For example, an angle with which one or more fluid streams are directed toward a thrombus may be selected or altered according to a pressure with which the inflatable shroud is inflated. Advantageously, the collapsed configuration can improve translation of the catheter during advancement and retraction, and the expanded configuration can improve illumination/imaging pathways during material removal.

FIG. 1F is similar to the embodiments depicted in FIGS. 1D and 1E, but further includes a plurality of imaging elements 108 (e.g., a camera, such as CCD camera, or CMOS camera) and/or illuminators 115 within an expandable housing 117 at the distal portion 104a of the elongated catheter 102. The imaging elements and illuminators may be collectively described as "visualization elements." The expandable housing 117 substantially surrounds the expandable chamber 109. The plurality of imaging elements 108 and/or illuminators 115 can be operably coupled to 1) a distal end, 2) an exterior surface, 3) interior surface, and/or 4) embedded within a wall of, the expandable housing 117. The plurality of imaging element 108 and/or illuminators 115 can be arranged in a variety of ways. For example, the arrangement can be a) individual, b) in pairs, c) triplets, d) quartets, e) quintets, and/or f) sextets. In some embodiments, at least one imaging element and/or illuminator 115 is steerable. In some embodiments, the expanded configuration of the expandable housing 117 can advantageously assist in seating an outer perimeter of the distal portion 104a against a lumen wall (e.g., forming a seal therewith). In some embodiments, the expandable housing 117 is generally annular in cross-section (e.g., cross-section in variation 1F-A). In some embodiments, the expandable housing 117 has a radially outermost wall that is generally undulating (e.g., cross-section in variation 1F-B). Regions 121 of the undulating outermost wall that are radially further from a central axis of the catheter can contact the vessel wall, while regions 123 that are radially closer to the central axis can provide a pathway for fluid flow. In some embodiments, maintaining fluid flow can advantageously promote continued perfusion for the patient, during thrombus removal.

In some embodiments, at least one vizualization element is steerable. Steering can be accomplished by an inflatable channel. In some embodiments, the inflatable channel for steering is the same as (or forms a portion of) an inflatable channel for inflating the expandable housing 117. In some embodiments, a separate (e.g., dedicated) inflatable channel is provided for steering. In various embodiments, any gas or fluid described herein for inflation of the inflatable shroud may be used for the inflatable channel for steering. In some embodiments, steering of the vizualization element may be (e.g., passively) responsive to pressure, for example the pressure within the inflatable shroud 117. In some embodiments, steering of the vizualization element may be via mechanical means, e.g., a wire.

In some embodiments, the system 100 can capture, macerate and/or fragment a thrombus using irrigation alone. FIG. 1G is similar to the embodiment depicted in FIG. 1E, but without a capture element 110. In the example of FIG. 1G, openings 139a-b of fluid delivery mechanism 124 are arranged to direct fluid streams 136a-b along a given path of travel. In some embodiments, at least two openings 139a-b (e.g., fluid ports) are arranged to direct fluid streams to intersect with one another (e.g., at fluid intersection 137). Advantageously, intersecting fluid streams can collide and impart increased forces to a portion of a thrombus that is near the point of collision. As used herein, "intersecting" does not necessarily mean physically intersecting. Intersecting is intended in its most general sense. Intersecting may include the fluid being directed towards a common region or volume as opposed to a specific point. Additionally or alternatively, the intersecting point or region may be within or behind the thrombus such that the fluid streams hit the target thrombus before they can physically intersect each other. The increased forces can be with respect to the forces imparted by similar fluid streams that contact the thrombus singly, that is, without any collision between fluid streams. In some embodiments, the openings 139a-b are arranged such that fluid streams are directed at least partially proximally (e.g., backward). In some embodiments, the openings 139a-b are arranged such that fluid streams are directed at an angle that is a) substantially normal to a central axis 141 of the chamber 109, or b) at least partially distally (e.g., toward distal opening). While intersection 137 is depicted near a central region of the expandable chamber 109, it will be appreciated that the intersection of the fluid streams can be arranged in a variety of locations within the chamber 109. Forces generated by the fluid streams 136a-b at the intersection 137 can be sufficient to 1) macerate/fragment a thrombus, as well as 2) urge the thrombus fragment(s) to be evacuated proximally along the catheter 102.

The system 100 can include a console 130 (best seen in FIG. 1B-shown schematically) including various components for controlling the operation of the system 100. For example, the console 130 can include the aspiration mechanism 140 and can be coupled to the collection container 142. The console 130 can also include a fluid source 144 that is fluidly coupled to the fluid delivery mechanism (e.g., fluid delivery mechanism 114 of FIG. 1D or fluid delivery mechanism 124 of FIG. 1E). The fluid source 144 can be configured to pressurize the fluid contained therein (e.g., saline) to a sufficiently high pressure for macerating thrombus. The console 130 can optionally include or be coupled with a gas source (not shown) that is fluidly coupled to a gas delivery mechanism (not shown) that is configured to inflate one or more components of the system.

The console 130 can also include a controller 146 for controlling the movement (e.g., rotational and/or longitudinal movement) of the capture element 110. In some embodiments, the consoles 130 also includes an actuation mechanism (e.g., a motor, cam, etc.—not shown) for actuating the movement of the capture element 110. Alternatively, the actuation mechanism can be located within, at, or near the proximal portion 104b of the elongated catheter 102, and the controller 146 can be operably coupled to the actuation mechanism to control the operation thereof.

The console 130 can include other electronic components 148 for powering and/or controlling operation of the system 100, such as a microcontroller, FPGA, ASIC, or other programmable component or system capable of storing and executing software and/or firmware that drives operation of the system 100 or a component thereof; memory such as RAM or ROM to store data and/or software/firmware; wireless communication hardware such as an antenna system configured to transmit via Bluetooth, Wi-Fi, or other protocols as would be understood by one of skill from the description herein; a display, monitor, or other user interface elements; and/or one or more sensors. For example, the electronic components 148 can be configured to control operation of the capture element 110, the fluid delivery mechanism (e.g., fluid delivery mechanism 114 of FIG. 1D or fluid delivery mechanism 124 of FIG. 1E), one or more sensors (e.g., sensor 113, imaging element 108 of FIG. 1C), the aspiration mechanism 140, the fluid source 144, and/or the controller 146.

The console 130 can be coupled to the proximal portion 104b of the elongated catheter 102. In some embodiments, the console 130 is coupled to the proximal portion 104b via a hub or adapter 150. The hub 150 can include multiple different connectors to operably couple the various components of the console 130 to the components of the elongated catheter 102. For example, the hub 150 can include a vacuum connection between the aspiration mechanism 140 and the lumen 106. The hub 150 can also include a fluid connection between the fluid source 144 and the fluid delivery mechanism (e.g., fluid delivery mechanism 114 of FIG. 1D or fluid delivery mechanism 124 of FIG. 1E). In some embodiments, the hub 150 includes one or more components (e.g., tubes, connectors, joints, etc.) configured to withstand high vacuum pressures and/or fluid pressures produced by the aspiration mechanism 140 and the fluid source 144, respectively. The hub 150 can also include an electronic connection between the controller 146 and an actuation mechanism for the capture element 110. The hub 150 can also electrically couple the electronic components 148 of the console 130 to other components of the system 100 (e.g., sensors).

In some embodiments, the system 100 is also configured to deliver one or more thrombolytic agents, such as a tissue plasminogen activator, a streptokinase, a urokinase, or a derivative or combination thereof. The thrombolytic agent(s) can be delivered from the elongated catheter 102 (e.g., through the lumen 106, a separate channel, or an opening in the distal portion 104a) prior to, concurrently with, or after capture and/or maceration of the thrombus. The thrombolytic agent(s) can be delivered locally to the site of the thrombus within the patient's blood vessel and/or can be delivered into the expandable chamber 109 to facilitate thrombus maceration.

As one of skill in the art will appreciate from the disclosure herein, various components of the thrombus removal systems described above can be omitted without deviating from the scope of the present technology. As discussed previously, for example, the present technology can be used and/or modified to remove other types of emboli that may occlude a blood vessel, such as fat, tissue, or a foreign substance. Further, although some embodiments herein are described in the context of thrombus removal from a pulmonary artery, the disclosed technology may be applied to removal of thrombi and/or emboli from other portions of the vasculature (e.g., in neurovascular, coronary, or peripheral applications). Likewise, additional components not explicitly described above may be added to the thrombus removal systems without deviating from the scope of the present technology. Accordingly, the systems described herein are not limited to those configurations expressly identified, but rather encompasses variations and alterations of the described systems.

EXAMPLES

Several aspects of the present technology are set forth in the following examples:

1. A method for removing a thrombus from a blood vessel of a patient, the method comprising:
   introducing a distal portion of an elongate catheter to a thrombus location in a blood vessel;
   drawing at least a section of the thrombus into the distal portion; and
   directing fluid from at least two different points toward the thrombus.

2. The method of example 1 wherein introducing the distal portion is into the blood vessel in a low-profile configuration, and wherein the method further comprises expanding the distal portion into a deployed configuration.

3. The method of example 2 wherein the drawing is into the distal portion using a capture element, and wherein the method further comprises expanding the capture element from the low-profile configuration to the deployed configuration.

4. The method of any one of examples 1-3 wherein the drawing is into the distal portion using a rotatable screw or auger.

5. The method of example 4, further comprising:

sensing a characteristic of the thrombus; and adjusting a rotation speed of the rotatable screw or auger based on the sensed characteristic.

6. The method of any one of examples 1-5, further comprising applying the fluid by one or more nozzles within the distal portion to form at least two fluid streams.

7. The method of example 6, further comprising directing the at least two fluid streams along intersecting paths.

8. The method of any one of examples 1-6 wherein the blood vessel comprises a pulmonary artery.

9. The method of any one of examples 1-8, further comprising, prior to the drawing, imaging the thrombus with an imaging element at the distal portion.

10. The method of example 9 wherein the imaging is through a fluid path.

11. The method of example 10, further comprising forming the fluid path using the fluid that is being directed from the at least two different points.

12. The method of any one of examples 1-11, further comprising aspirating fragments of the thrombus to a proximal portion of the elongate catheter.

13. The method of any one of examples 1-11, further comprising engaging the thrombus with the distal portion to form a seal against the thrombus.

14. A system for removing a thrombus from a blood vessel of a patient, the system comprising:

an elongated catheter device having— a distal portion configured to be positioned within the blood vessel of the patient, the distal portion comprising at least two fluid ports configured to direct respective fluid streams along respective paths that intersect, a proximal portion configured to be positioned external to the patient, and a lumen extending therebetween;

an aspiration mechanism positioned external to the patient and fluidly coupled with the lumen, the aspiration mechanism configured to reduce a pressure at the distal portion (a) to engage the thrombus therewith and/or (b) to draw the thrombus and/or thrombus fragments proximally; and a fluid delivery mechanism configured to supply fluid through the elongated catheter device to the at least two fluid ports.

15. The system of example 14 wherein the fluid delivery mechanism comprises at least two structures configured to fluidly couple with the at least two fluid ports.

16. The system of example 14 wherein the at least two fluid ports are arranged such that, when delivered, the respective fluid streams intersect within an expandable housing at the distal portion.

17. The system of example 14 wherein at least one fluid port of the at least two fluid ports is arranged to deliver a respective fluid jet proximally.

18. The system of example 14 wherein the at least one fluid port is arranged to deliver the respective fluid jet toward a central axis of the elongated catheter device.

19. The system of example 14, further comprising an imaging element and/or an illumination source disposed within an expandable housing at the distal portion.

20. The system of example 19 wherein the fluid delivery mechanism is further configured to apply the fluid to provide an optical path for the imaging element and/or illumination source.

21. A system for removing a thrombus from a blood vessel of a patient, the system comprising:

an elongated catheter having a distal portion configured to be positioned within the blood vessel of the patient, a proximal portion configured to be positioned external to the patient, and a lumen extending therebetween;

a capture element at the distal portion and configured to engage the thrombus;

a fluid delivery mechanism within the lumen and configured to apply fluid to at least partially fragment the thrombus; and an aspiration mechanism fluidly coupled to the lumen and configured to aspirate the fragmented thrombus.

22. The system of example 21 wherein the capture element comprises a rotatable screw or auger.

23. The system of example 21 or example 22 wherein the capture element is positioned at least partially within the lumen.

24. The system of any one of examples 21-23 wherein the capture element is generally conical in axial cross-section.

25. The system of any one of examples 21-23 wherein the capture element is expandable.

26. The system of example 25 wherein at least a portion of the capture element is inflatable.

27. The system of any one of examples 21-26 wherein the capture element is configured to move relative to the distal portion to draw the thrombus into the lumen.

28. The system of any one of examples 21-26 wherein the capture element comprises a sensing element configured to measure a characteristic of the thrombus.

29 The system of any one of examples 21-28 wherein the fluid delivery mechanism is proximal to the capture element.

30. The system of any one of examples 21-29 wherein the fluid is pressurized saline.

31. The system of any one of examples 21-30 wherein the distal portion includes an expandable chamber transformable between a low-profile configuration and a deployed configuration.

32. The system of example 31 wherein the elongated catheter includes an intermediate portion between the proximal and distal portions, and wherein when in the deployed configuration, the expandable chamber has a cross-sectional dimension greater than a cross-sectional dimension of the intermediate portion.

33. The system of example 31 wherein the expandable chamber has a cross-sectional dimension that varies along its axial length.

34 The system of example 33 wherein the expandable chamber is generally funnel-shaped.

35. The system of example 31 wherein the expandable chamber comprises at least one wall that is expandable by fluid or gas inflation.

36. The system of any of the examples 31-35 wherein the capture element is configured to withdraw the thrombus into the expandable chamber.

37. The system of any one of examples 31-36 wherein the fluid delivery mechanism is within the expandable chamber.

38. The system of any one of examples 21-37, further comprising an imaging element at the distal portion and configured to visualize at least a portion of the thrombus.

39. The system of example 38 wherein the fluid delivery mechanism is further configured to apply the fluid to provide an optical path for the imaging element.

40. The system of example 21 wherein the fluid is optically transparent in a visible spectrum.

41. The system of any one of examples 38-40, further comprising an illumination source at the distal portion.

42. The system of example 41 wherein at least one of the imaging element and the illumination source is steerable.

43. The system of example 42, further comprising an inflatable channel having a distal portion that is coupled with the at least one of the imaging element and the illumination source, and a proximal portion that is fluidly coupled with the fluid delivery mechanism, wherein the inflatable channel.

44. The system any one of examples 21-43, further comprising a console operably coupled to the proximal portion of the elongated catheter.

45. The system of example 44 wherein the console is configured to control one or more of the imaging element, the capture element, the fluid delivery mechanism, or the aspiration mechanism.

46. A method for treating a patient, the method comprising:
    intravascularly delivering a distal portion of a catheter to a location adjacent to a thrombus within vasculature of the patient;
    generating image data of the vasculature and/or the thrombus via an imaging element carried by the distal portion of the catheter;
    drawing at least a section of the thrombus into the distal portion; and
    delivering fluid having a selected pressure and selected flow rate via one or more openings at the distal portion of the catheter to at least partially fragment the thrombus,
    wherein the selected pressure and/or the selected flow rate are based, at least in part, on the image data.

47. The method of example 46 wherein generating image data comprises generating image data before, during, and/or after at least partially fragmenting the thrombus.

48. The method of example 46 wherein the image data comprises information regarding a type and/or characteristic of the thrombus, and wherein the selected pressure and/or selected flow rate are based, at least in part, on the type and/or characteristic of the thrombus.

49. A method for treating a patient, the method comprising:
    delivering a distal portion of a catheter to a location proximate a thrombus within vasculature of the patient;
    generating image data of the thrombus via an imaging element carried by the distal portion of the catheter; and
    engaging the thrombus with a capture element at the distal portion of the catheter, wherein one or more properties of the capture element are based, at least in part, on the image data of the thrombus.

50. The method of example 49 wherein generating image data comprises generating data regarding the type of thrombus.

51. The method of example 49 wherein the one or more properties of the capture element comprises thread size, thread pitch, and/or durometer.

CONCLUSION

The above detailed description of embodiments of the technology are not intended to be exhaustive or to limit the technology to the precise forms disclosed above. Although specific embodiments of, and examples for, the technology are described above for illustrative purposes, various equivalent modifications are possible within the scope of the technology as those skilled in the relevant art will recognize. For example, although steps are presented in a given order, alternative embodiments may perform steps in a different order. The various embodiments described herein may also be combined to provide further embodiments.

From the foregoing, it will be appreciated that specific embodiments of the technology have been described herein for purposes of illustration, but well-known structures and functions have not been shown or described in detail to avoid unnecessarily obscuring the description of the embodiments of the technology. Where the context permits, singular or plural terms may also include the plural or singular term, respectively.

Unless the context clearly requires otherwise, throughout the description and the examples, the words "comprise," "comprising," and the like are to be construed in an inclusive sense, as opposed to an exclusive or exhaustive sense; that is to say, in the sense of "including, but not limited to." As used herein, the terms "connected," "coupled," or any variant thereof, means any connection or coupling, either direct or indirect, between two or more elements; the coupling of connection between the elements can be physical, logical, or a combination thereof. Additionally, the words "herein," "above," "below," and words of similar import, when used in this application, shall refer to this application as a whole and not to any particular portions of this application. Where the context permits, words in the above Detailed Description using the singular or plural number may also include the plural or singular number respectively. As used herein, the phrase "and/or" as in "A and/or B" refers to A alone, B alone, and A and B. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with some embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

We claim:

1. A system for removing a thrombus from a blood vessel of a patient, the system comprising:
    an elongated catheter having a distal portion configured to be positioned within the blood vessel of the patient, a proximal portion configured to be positioned external to the patient, and an aspiration lumen extending therebetween;
    a chamber at the distal portion, the chamber having an outer surface that defines a distal opening;
    an aspiration mechanism fluidly coupled to the aspiration lumen and configured to reduce a pressure within the chamber to engage the thrombus within the distal opening of the chamber;
    a first fluid port and a second fluid port disposed within the chamber and surrounded by the outer surface of the chamber, the first fluid port having a first axis, the second fluid port having a second axis, wherein the first axis intersects with the second axis at a fluid intersection within the chamber, the first fluid port and the second fluid port being configured to direct respective fluid streams along the first axis and the second axis that collide with each other at the fluid intersection, wherein the fluid streams are configured to cut and at least partially fragment the thrombus engaged within the chamber such that the aspiration lumen can aspirate the at least partially fragmented thrombus.

2. The system of claim 1, further comprising a sensing element at the distal portion configured to measure a characteristic of the thrombus.

3. The system of claim 1, wherein the chamber comprises an expandable chamber that is transformable between a low-profile configuration and a deployed configuration.

4. The system of claim 3 wherein the elongated catheter includes an intermediate portion between the proximal and distal portions, and wherein when in the deployed configuration, the expandable chamber has a cross-sectional dimension greater than a cross-sectional dimension of the intermediate portion.

5. The system of claim 3 wherein the expandable chamber has a cross-sectional dimension that varies along its axial length.

6. The system of claim 5 wherein the expandable chamber is generally funnel-shaped.

7. The system of claim 3 wherein the expandable chamber comprises at least one wall that is expandable by fluid or gas inflation.

8. The system of claim 1, further comprising a fluid delivery mechanism configured to supply fluid through the elongated catheter to the first fluid port and the second fluid port.

9. The system of claim 8, further comprising one or more fluid lumens configured to fluidly couple the fluid delivery mechanism to the first fluid port and the second fluid port.

10. The system of claim 9, wherein the one or more fluid lumens are distinct from the lumen.

11. The system of claim 1, wherein the fluid streams are directed proximally relative to a longitudinal axis of the elongated catheter.

12. The system of claim 1, wherein the fluid streams are directed distally relative to a longitudinal axis of the elongated catheter.

13. The system of claim 1, wherein the fluid streams are directed substantially normal to a longitudinal axis of the elongated catheter.

14. The system of claim 1, wherein the fluid streams are directed at a selected pressure such that the fluid streams dissipates prior to impacting an opposing wall of the distal portion.

15. A system for removing a thrombus from a blood vessel of a patient, the system comprising:

an elongated catheter having a distal portion configured to be positioned within the blood vessel of the patient, a proximal portion configured to be positioned external to the patient, and a lumen extending therebetween;

a chamber at the distal portion, the chamber having an outer surface that defines a distal opening configured to engage the thrombus;

a first fluid port and a second fluid port disposed within the chamber and surrounded by the outer surface of the chamber, the first fluid port arranged to direct a first fluid stream along a first axis, the second fluid port arranged to direct a second fluid stream along a second axis that intersects with the first axis at a fluid intersection within the chamber, wherein the first and second fluid streams are configured to cut and at least partially fragment the thrombus; and an aspiration mechanism fluidly coupled to the lumen and configured to aspirate the at least partially fragmented thrombus.

*   *   *   *   *